(12) United States Patent
Clark et al.

(10) Patent No.: US 7,576,076 B2
(45) Date of Patent: Aug. 18, 2009

(54) MODIFIED PYRIMIDINE GLUCOCORTICOID RECEPTOR MODULATORS

(75) Inventors: Robin D. Clark, Lawai, HI (US); Nicolas C. Ray, Harlow (GB); Karen Williams, Harlow (GB); Peter H. Crackett, Harlow (GB); Gwen Hickin, Harlow (GB); David A. Clark, Harlow (GB)

(73) Assignee: Corcept Therapeutics, Inc., Menlo Park, CA (US)

( * ) Notice: Subject to any disclaimer, the term of this patent is extended or adjusted under 35 U.S.C. 154(b) by 416 days.

(21) Appl. No.: 11/174,096

(22) Filed: Jun. 29, 2005

(65) Prior Publication Data

US 2006/0025405 A1 Feb. 2, 2006

Related U.S. Application Data

(60) Provisional application No. 60/585,018, filed on Jul. 2, 2004.

(51) Int. Cl.
*A01N 43/62* (2006.01)
*A61K 31/50* (2006.01)
*A61K 31/497* (2006.01)
*A61K 31/501* (2006.01)
*A61K 31/505* (2006.01)
*C07D 403/00* (2006.01)
*C07D 401/00* (2006.01)
*C07D 405/00* (2006.01)
*C07D 409/00* (2006.01)
*C07D 411/00* (2006.01)
*C07D 413/00* (2006.01)
*C07D 417/00* (2006.01)
*C07D 419/00* (2006.01)
*C07D 243/08* (2006.01)

(52) U.S. Cl. .................. 514/218; 514/252.14; 514/269; 544/295; 544/310; 540/575

(58) Field of Classification Search ........................ None
See application file for complete search history.

(56) References Cited

U.S. PATENT DOCUMENTS 6,852,719 B2 * 2/2005 Liu et al. .................. 514/236.2

FOREIGN PATENT DOCUMENTS

EP 0037495 A1 10/1981
EP 0369627 A2 5/1990
EP 0722732 A1 7/1996
JP 06128238 A 5/1994
JP 10017555 A 1/1998
WO WO02/44120 A1 6/2002
WO WO03/084935 A2 10/2003

OTHER PUBLICATIONS

Dorwald F. A. Side Reactions in Organic Synthesis, 2005, Wiley: VCH, Weinheim pg. IX of Preface.*
Teutsch G., et al. "Design of ligands for the glucocortoid and progestin receptors", *Biochemical Society Transactions* (1991) 19(4):901-908.
Fukazawa, Nobuyuki, et al. "6-Amino-5-methyluracil derivatives and their use as thymidine phosphorylase inhibitors and neovascularization inhibitors", XP002355358; Database CA 'Online'; Chemical Abstracts Service, Columbus, OH, US; Database accession No. 1998:59356, Abstract.
Bhuyan, Pulak J., et al. "Studies on Uracils: Synthesis of Novel Uracil Analogs via 1,5- and 1,6-Intramolecular Cycloadditional Reactions", XP002355359; Database CA 'Online'; Chemical Abstracts Service, Columbus, OH, US; Database accession No. 1998:598911, Abstract.

* cited by examiner

*Primary Examiner*—James O Wilson
*Assistant Examiner*—Jeffrey H Murray
(74) *Attorney, Agent, or Firm*—Townsend and Townsend and Crew LLP

(57) ABSTRACT

The present invention provides a compound having the formula:

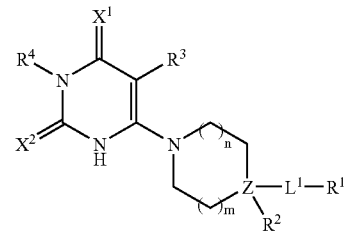

wherein, n and m are 1; $X^1$ and $X^2$ are O; $R^1$ is a member selected from unsubstituted phenyl and substituted phenyl; $R^2$ is a member selected from hydrogen, —CN, —O $R^{2A}$, -$L^{2A}$—C(O)$R^{2B}$, -$L^{2B}$—S(O)$_2R^{2C}$; $R^3$ is a member selected from unsubstituted benzyl and substituted benzyl; $R^4$ is a member selected from hydrogen and substituted or unsubstituted alkyl, wherein if $R^4$ is methyl, then -$L^1$-$R^1$ is not benzyl or —C(O)—O—CH$_2$—CH$_3$; and $L^1$ is a bond; and compositions and methods of using the compounds as glucocorticoid receptor modulators.

12 Claims, No Drawings

MODIFIED PYRIMIDINE GLUCOCORTICOID RECEPTOR MODULATORS

CROSS-REFERENCES TO RELATED APPLICATIONS

This application claims the benefit of U.S. Provisional Patent Application No. 60/585,018, filed Jul. 2, 2004, which is incorporated herein by reference in its entirety for all purposes.

BACKGROUND OF THE INVENTION

In most species, including man, the physiological glucocorticoid is cortisol (hydrocortisone). Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR). In man, glucocorticoid receptors are present in two forms: a ligand-binding GR-alpha of 777 amino acids; and, a GR-beta isoform which differs in only the last fifteen amino acids. The two types of GR have high affinity for their specific ligands, and are considered to function through the same transduction pathways.

The biologic effects of cortisol, including those caused by hypercortisolemia, can be modulated at the GR level using receptor modulators, such as agonists, partial agonists and antagonists. Several different classes of agents are able to block the physiologic effects of GR-agonist binding. These antagonists include compositions which, by binding to GR, block the ability of an agonist to effectively bind to and/or activate the GR. One such known GR antagonist, mifepristone, has been found to be an effective anti-glucocorticoid agent in humans (Bertagna (1984) *J. Clin. Endocrinol. Metab.* 59:25). Mifepristone binds to the GR with high affinity, with a dissociation constant ($K_d$) of $10^{-9}$ M (Cadepond (1997) *Annu. Rev. Med.* 48:129).

Patients with some forms of psychiatric illnesses have been found to have increased levels of cortisol (Krishnan (1992) *Prog. Neuro-Psychophannacol. & Biol. Psychiat.* 16:913-920). For example, some depressed individuals can be responsive to treatments which block the effect of cortisol, as by administering GR antagonists (Van Look (1995) *Human Reproduction Update* 1: 19-34). In one study, a patient with depression secondary to Cushing's Syndrome (hyperadrenocorticism) was responsive to a high dose, up to 1400 mg per day, of GR antagonist mifepristone (Nieman (1985) *J. Clin Endocrinol. Metab.* 61:536). Another study which used mifepristone to treat Cushing's syndrome found that it improved the patients' conditions, including their psychiatric status (Chrousos, pp 273-284, In: Baulieu, ed. *The Antiprogestin Steroid RU 486 and Human Fertility Control*. Plenum Press, New York (1989), Sartor (1996) *Clin. Obstetrics and Gynecol.* 39:506-510).

Psychosis has also been associated with Cushing's syndrome (Gerson (1985) *Can. J. Psychiatry* 30:223-224; Saad (1984) *Am. J. Med.* 76:759-766). Mifepristone has been used to treat acute psychiatric disturbances secondary to Cushing's syndrome. One study showed that a relatively high dose of mifepristone (400 to 800 mg per day) was useful in rapidly reversing acute psychosis in patients with severe Cushing Syndrome due to adrenal cancers and ectopic secretion of ACTH from lung cancer (Van der Lely (1991) *Ann. Intern. Med.* 114:143; Van der Lely (1993) *Pharmacy World & Science* 15:89-90; Sartor (1996) supra).

A treatment for psychosis or the psychotic component of illnesses, such as psychotic major depression, has recently been discovered (Schatzberg et al., U.S. Pat. No. 6,150,349). The treatment includes administration of an amount of a glucocorticoid receptor antagonist effective to ameliorate the psychosis. The psychosis may also be associated with psychotic major depression, schizoaffective disorder, Alzheimer's Disease and cocaine addiction.

Thus, there exists a great need for a more effective and safer treatment for illnesses and conditions associated with the glucocorticoid receptors, including psychotic major depression. The present invention fulfills these and other needs.

SUMMARY OF THE INVENTION

In one aspect, the present invention provides a GR modulator compound having the formula:

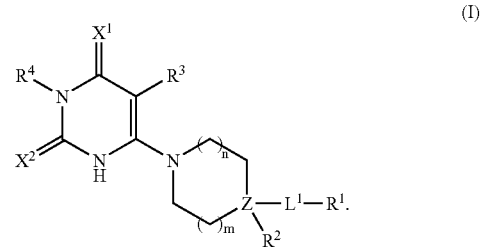

(I)

In Formula (I), m and n are integers independently selected from 0 to 2. $X^1$ and $X^2$ are independently selected from O and S.

Z is selected from C and N. If Z is N, however, then $R^2$ is absent.

$R^1$ is selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

$R^2$ is selected from hydrogen, substituted or unsubstituted alkyl, substituted or unsubstituted heteroalkyl, —CN, —$OR^{2A}$, -$L^{2A}$—C(O)$R^{2B}$, and -$L^{2B}$—S(O)$_2R^{2C}$. $L^{2A}$ and $L^{2B}$ are independently selected from a bond and —NH—.

$R^{2A}$ is a member selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{2B}$ and $R^{2C}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —$NR^{2D}R^{2E}$, and —$OR^{2F}$.

$R^{2D}$, $R^{2E}$, and $R^{2F}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

$R^3$ is selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^3$ is selected from substituted or unsubstituted arylalkyl, substituted or unsubstituted heteroarylalkyl, substituted or unsubstituted cycloalkyl-alkyl, substituted or unsubstituted heterocycloalkyl-alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

$R^4$ is selected from hydrogen and substituted or unsubstituted alkyl. In an exemplary embodiment, where $R^4$ is methyl, -$L^1$-$R^1$ is not benzyl or —C(O)—O—CH$_2$—CH$_3$. In another exemplary embodiment, $R^4$ is selected from hydrogen and substituted or unsubstituted $C_2$-$C_{20}$ alkyl. $R^4$ may also be selected from hydrogen and substituted or unsubstituted higher alkyl.

$L^1$ is selected from a bond, —O—, —S—, —SO$_2$—, —C(O)N—, —C(O)O—, —C(O)—, —NR$^{1.4}$—, substituted or unsubstituted alkylene, and substituted or unsubstituted heteroalkylene. $R^{1.4}$ is selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In another aspect, the present invention provides methods of treating a disorder or condition through modulating a glucocorticoid receptor. The method includes administering to a subject in need of such treatment, an effective amount of the compound of Formula (I).

In another aspect, the present invention provides methods of treating a disorder or condition through antagonizing a glucocorticoid receptor. The method includes administering to a subject in need of such treatment, an effective amount of the compound of Formula (I).

In another aspect, the present invention provides methods of modulating a glucocorticoid receptor including the steps of contacting a glucocorticoid receptor with the compound of Formula (I) and detecting a change in the activity of the glucocorticoid receptor.

In another aspect, the present invention provides a pharmaceutical composition. The pharmaceutical composition includes a pharmaceutically acceptable excipient and a compound of having the formula:

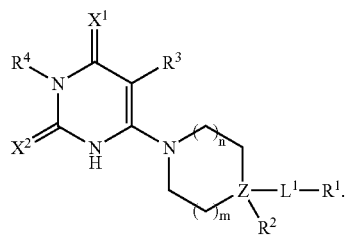

(I)

Where a pharmaceutical composition includes a compound of Formula (I), n, m, Z. $X^1$, $X^2$, $L^1$, $R^1$, $R^2$, and $R^4$ are as defined above. $R^3$ is selected from substituted or unsubstituted arylalkyl, substituted or unsubstituted heteroarylalkyl, substituted or unsubstituted cycloalkyl-alkyl, substituted or unsubstituted heterocycloalkyl-alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

DETAILED DESCRIPTION OF THE INVENTION

Abbreviations and Definitions

The abbreviations used herein have their conventional meaning within the chemical and biological arts.

Where moieties are specified by their conventional chemical formulae, written from left to right, they equally encompass the chemically identical moieties that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkyl, as exemplified, but not limited, by —CH$_2$CH$_2$CH$_2$CH$_2$—. Typically, an alkyl (or alkylene) group will have from 1 to 24 carbon atoms, including those groups having 10 or fewer carbon atoms. A "lower alkyl" or "lower alkylene" is a shorter chain alkyl or alkylene group, generally having eight or fewer carbon atoms.

The terms "alkoxy," "alkylamino," and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and a heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—

$-CH_2-$ and $-CH_2-S-CH_2-CH_2-NH-CH_2-$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $-C(O)_2R'-$ represents both $-C(O)_2R'-$ and $-R'C(O)_2-$. As described above, heteroalkyl groups, as used herein, include those groups that are attached to the remainder of the molecule through a heteroatom, such as $-C(O)R'$, $-C(O)NR'$, $-NR'R"$, $-OR'$, $-SR'$, and/or $-SO_2R'$. Where "heteroalkyl" is recited, followed by recitations of specific heteroalkyl groups, such as $-NR'R"$ or the like, it will be understood that the terms heteroalkyl and $-NR'R"$ are not redundant or mutually exclusive. Rather, the specific heteroalkyl groups are recited to add clarity. Thus, the term "heteroalkyl" should not be interpreted herein as excluding specific heteroalkyl groups, such as $-NR'R"$ or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituent moieties for each of the above noted aryl and heteroaryl ring systems may be selected from the group of acceptable substituent moieties described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

Each of the above terms (e.g., "alkyl," "heteroalkyl," "aryl" and "heteroaryl") are meant to include both substituted and unsubstituted forms of the indicated radical. Preferred substituent moieties for each type of radical are provided below.

Substituent moieties for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: $-OR'$, $=O$, $=NR'$, $=N-OR'$, $-NR'R"$, $-SR'$, -halogen, $-SiR'R"R'''$, $-OC(O)R'$, $-C(O)R'$, $-CO_2R'$, $-CONR'R"$, $-OC(O)NR'R"$, $-NR"C(O)R'$, $-NR'-C(O)NR"R'''$, $-NR"C(O)_2R'$, $-NR-C(NR'R"R''')=NR""$, $-NR-C(NR'R")=NR'''$, $-S(O)R'$, $-S(O)_2R'$, $-S(O)_2NR'R"$, $-NRSO_2R'$, $-CN$ and $-NO_2$ in a number ranging from zero to (2m'+1), where m' is the total number of carbon atoms in such radical. R', R", R''' and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R''' and R"" groups when more than one of these groups is present. When R' and R" are attached to the same nitrogen atom, they can be combined with the nitrogen atom to form a 4-, 5-, 6-, or 7-membered ring. For example, $-NR'R"$ is meant to include, but not be limited to, 1-pyrrolidinyl and 4-morpholinyl. From the above discussion of substituent moieties, one of skill in the art will understand that the term "alkyl" is meant to include groups including carbon atoms bound to groups other than hydrogen groups, such as haloalkyl (e.g., $-CF_3$ and $-CH_2CF_3$) and acyl (e.g., $-C(O)CH_3$, $-C(O)CF_3$, $-C(O)CH_2OCH_3$, and the like).

Similar to the substituent moieties described for the alkyl radical, substituent moieties for the aryl and heteroaryl groups are varied and may be selected from, for example: halogen, $-OR'$, $-NR'R"$, $-SR'$, -halogen, $-SiR'R"R'''$, $-OC(O)R'$, $-C(O)R'$, $-CO_2R'$, $-CONR'R"$, $-OC(O)NR'R"$, $-NR"C(O)R'$, $-NR'-C(O)NR"R'''$, $-NR"C(O)_2R'$, $-NR-C(NR'R"R''')=NR""$, $-NR-C(NR'R")=NR'''$, $-S(O)R'$, $-S(O)_2R'$, $-S(O)_2NR'R"$, $-NRSO_2R'$, $-CN$ and $-NO_2$, $-R'$, $-N_3$, $-CH(Ph)_2$, fluoro($C_1$-$C_4$)alkoxy, and fluoro($C_1$-$C_4$)alkyl, in a number ranging from zero to the total number of open valences on the aromatic ring system; and where R', R", R''' and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R''' and R"" groups when more than one of these groups is present.

Two of the substituent moieties on adjacent atoms of the aryl or heteroaryl ring may optionally form a ring of the formula -T-C(O)-(CR')$_q$-U-, wherein T and U are independently $-NR-$, $-O-$, $-CRR'-$ or a single bond, and q is an integer of from 0 to 3. Alternatively, two of the substituent moieties on adjacent atoms of the aryl or heteroaryl ring may optionally be replaced with a substituent of the formula -A-$(CH_2)_r$-B—, wherein A and B are independently —CR'—, —O—, —NR—, —S—, —S(O)—, —S(O)$_2$—, —S(O)2NR'— or a single bond, and r is an integer of from 1 to 4. One of the single bonds of the new ring so formed may optionally be replaced with a double bond. Alternatively, two of the substituent moieties on adjacent atoms of the aryl or heteroaryl ring may optionally be replaced with a substituent of the formula —(CR')$_s$-X'—(C"R''')$_d$-, where s and d are independently integers of from 0 to 3, and X' is —O—, —NR'—, —S—, —S(O)—, —S(O)2—, or —S(O)$_2$NR'—. The substituent moieties R, R', R" and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

The term "pharmaceutically acceptable salts" is meant to include salts of the active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers and individual isomers are encompassed within the scope of the present invention. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

Where two groups are "optionally joined together to form a ring," the two groups are covalently bonded together with the atom or atoms to which the two groups are joined to form a substituted or unsubstituted aryl, a substituted or unsubstituted heteroaryl, a substituted or unsubstituted cycloalkyl, or a substituted or unsubstituted heterocycloalkyl ring.

The terms "arylalkyl," "heteroarylalkyl," "cycloalkyl-alkyl," and "heterocycloalkyl-alkyl," as used herein, refer to an aryl, heteroaryl, cycloalkyl and heterocycloalkyl, respectively, attached to the remainder of the molecule via an alkylene group. Where an "arylalkyl," "heteroarylalkyl," "cycloalkyl-alkyl," or "heterocycloalkyl-alkyl" is substituted, one or more substituent moieties may be covalently bonded to the alkylene moiety and/or the aryl, heteroaryl, cycloalkyl and heterocycloalkyl moieties, respectively. A "$C_1$-$C_{20}$" arylalkyl, heteroarylalkyl, cycloalkyl-alkyl, or heterocycloalkyl-alkyl, are moieties in which a $C_1$-$C_{20}$ alkylene links an aryl, heteroaryl, $C_4$-$C_8$ cycloalkyl, and 4 to 8 membered heterocycloalkyl, respectively, to the remainder of the molecule. A "$C_1$-$C_8$" arylalkyl, heteroarylalkyl, cycloalkyl-alkyl, or heterocycloalkyl-alkyl, are moieties in which a $C_1$-$C_8$ alkylene links an aryl, heteroaryl, $C_5$-$C_7$ cycloalkyl, and 5 to 7 membered heterocycloalkyl, respectively, to the remainder of the molecule A "substituent group," as used herein, means a group selected from the following moieties:
(A) —OH, —NH$_2$, —SH, —CN, —CF$_3$, oxy, halogen, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, and heteroaryl, substituted with at least one substituent selected from:
(i) oxy, —OH, —NH$_2$, —SH, —CN, —CF$_3$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:
(a) oxy, —OH, —NH$_2$, —SH, —CN, —CF$_3$, halogen, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, or heteroaryl, substituted with at least one substituent selected from oxy, —OH, —NH$_2$, —SH, —CN, —CF$_3$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

The term "cortisol" refers to a family of compositions also referred to as hydrocortisone, and any synthetic or natural analogues thereof.

The term "glucocorticoid receptor" ("GR") refers to a family of intracellular receptors also referred to as the cortisol receptor, which specifically bind to cortisol and/or cortisol analogs (e.g. dexamethasone). The term includes isoforms of GR, recombinant GR and mutated GR.

The term "glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" refers to any composition or compound which inhibits any biological response associated with the binding of a GR to an agonist. By "specific," we intend the drug to preferentially bind to the GR rather than another nuclear receptors, such as mineralocorticoid receptor (MR) or progesterone receptor (PR).

A patient "not otherwise in need of treatment with a glucocorticoid receptor modulator" is a patient who is not suffering from a condition which is known in the art to be effectively treatable with glucocorticoid receptor modulators. Conditions known in the art to be effectively treatable with glucocorticoid receptor modulators include diabetes, Cushing's disease, drug withdrawal, psychosis, dementia, stress disorders, psychotic major depression, as well as those described below.

The term "treating" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the methods of the invention successfully treat a patient's delirium by decreasing the incidence of disturbances in consciousness or cognition.

The term "higher alkyl" refers to those alkyl groups having at least six carbon atoms. The term "lower alkyl" refers to those alkyl groups having from one to five carbon atoms.

Description of the Embodiments

I. Glucocorticoid Receptor Modulators

It has now been discovered that modified pyrimidine compounds are potent modulators of glucocorticoid receptors ("GR"). GR modulators (also referred to herein as compounds of the present invention) typically act as agonists, partial agonists or antagonists of GR thereby affecting a wide array of cellular functions, physiological functions and disease states.

Cortisol acts by binding to an intracellular glucocorticoid receptor. In humans, glucocorticoid receptors are present in two forms: a ligand-binding GR-alpha of 777 amino acids; and, a GR-beta isoform that differs in only the last fifteen amino acids. The two types of GR have high affinity for their specific ligands, and are considered to function through the same transduction pathways.

GR modulators are typically efficacious agents for influencing important cellular and physiological functions such as carbohydrate, protein and lipid metabolism; electrolyte and water balance; and functions of the cardiovascular system, kidney, central nervous system, immune system, skeletal muscle system and other organ and tissue systems. GR modulators may also affect a wide variety of disease states, such as obesity, diabetes, cardiovascular disease, hypertension, Syndrome X, depression, anxiety, glaucoma, human immunodeficiency virus (HIV) or acquired immunodeficiency syndrome (AIDS), neurodegeneration (e.g. Alzheimer's disease and Parkinson's disease), cognition enhancement, Cushing's Syndrome, Addison's Disease, osteoperosis, frailty, inflammatory diseases (e.g., osteoarthritis, rheumatoid arthritis, asthma and rhinitis), adrenal function-related ailments, viral infection, immunodeficiency, immunomodulation, autoimmune diseases, allergies, wound healing, compulsive behavior, multi-drug resistance, addiction, psychosis associated with depression, anorexia, cahexia, post-traumatic stress syndrome, post-surgical bone fracture, medical catabolism, and muscle frailty.

In one aspect, the present invention provides a GR modulator compound having the formula:

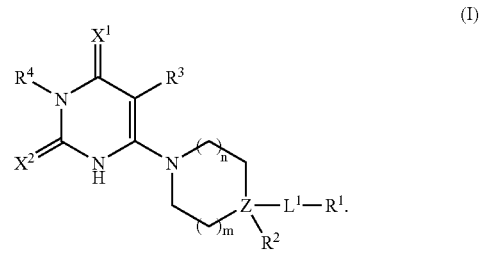

(I)

In Formula (I), m and n are integers independently selected from 0 to 2. X$^1$ and X$^2$ are independently selected from O and S.

Z is selected from C and N. If Z is N, however, then $R^2$ is absent.

$R^1$ is selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

$R^2$ is selected from hydrogen, substituted or unsubstituted alkyl, substituted or unsubstituted heteroalkyl, —CN, —OR$^{2A}$, -L$^{2A}$—C(O)R$^{2B}$, and -L$^{2B}$—S(O)$_2$R$^{2C}$. L$^{2A}$ and L$^{2B}$ are independently selected from a bond and —NH—.

$R^{2A}$ is a member selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{2B}$ and $R^{2C}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —NR$^{2D}$R$^{2E}$, and —OR$^{2F}$.

$R^{2D}$, $R^{2E}$, and $R^{2F}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

$R^3$ is selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^3$ is selected from substituted or unsubstituted arylalkyl, substituted or unsubstituted heteroarylalkyl, substituted or unsubstituted cycloalkyl-alkyl, substituted or unsubstituted heterocycloalkyl-alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

$R^4$ is selected from hydrogen and substituted or unsubstituted alkyl. In an exemplary embodiment, where $R^4$ is methyl, -L$^1$-R$^1$ is not benzyl or —C(O)—O—CH$_2$—CH$_3$. In another exemplary embodiment, $R^4$ is selected from hydrogen and substituted or unsubstituted C$_2$-C$_{20}$ alkyl. $R^4$ may also be selected from hydrogen and substituted or unsubstituted higher alkyl.

$L^1$ is selected from a bond, —O—, —S—, —SO$_2$—, —C(O)N—, —C(O)O—, —C(O)—, —NR$^{1A}$-, substituted or unsubstituted alkylene, and substituted or unsubstituted heteroalkylene. $R^{1A}$ is selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, each substituted group described above in the compound of Formula (I) is substituted with at least one substituent group. The term "substituent group," as used herein, is defined in detail above in the "Abbreviations and Definitions" section. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted arylalkyl, substituted heteroarylalkyl, substituted cycloalkyl-alkyl, and/or substituted heterocycloalkyl-alkyl described above in the compound of Formula (I) are substituted with at least one substituent group. In other embodiments, at least one or all of these groups are substituted with at least one size-limited group. Alternatively, at least one or all of these groups are substituted with at least one lower substituent group. Size-limited groups and lower substituent groups are both defined in detail above in the "Abbreviations and Definitions" section.

In other exemplary embodiments, each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, each substituted or unsubstituted heterocycloalkyl is a substituted or unsubstituted 4 to 8 membered heterocycloalkyl, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted arylalkyl is a substituted or unsubstituted C$_1$-C$_{20}$ arylalkyl, each substituted or unsubstituted heteroarylalkyl is a substituted or unsubstituted C$_1$-C$_{20}$ heteroarylalkyl, each substituted or unsubstituted cycloalkyl-alkyl is a substituted or unsubstituted C$_1$-C$_{20}$ cycloalkyl-alkyl, and/or each substituted or unsubstituted heterocycloalkyl-alkyl is a substituted or unsubstituted C$_1$-C$_{20}$ heterocycloalkyl-alkyl.

Alternatively, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, each substituted or unsubstituted heterocycloalkyl is a substituted or unsubstituted 5 to 7 membered heterocycloalkyl, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted arylalkyl is a substituted or unsubstituted C$_1$-C$_8$ arylalkyl, each substituted or unsubstituted heteroarylalkyl is a substituted or unsubstituted C$_1$-C$_8$ heteroarylalkyl, each substituted or unsubstituted cycloalkyl-alkyl is a substituted or unsubstituted C$_1$-C$_8$ cycloalkyl-alkyl, and/or each substituted or unsubstituted heterocycloalkyl-alkyl is a substituted or unsubstituted C$_1$-C$_8$ heterocycloalkyl-alkyl.

In some embodiments, n is 0 and m is 2. Alternatively, m and n are both 1 and Z is N. $X^1$ and $X^2$ may both be O. In some embodiments, where Z is N, $L^1$ is not O or S.

$R^1$ may be selected from unsubstituted aryl, and aryl substituted with a lower substituent. $R^1$ may also be selected from unsubstituted phenyl, and phenyl substituted with a lower substituent. In some embodiments, $R^1$ is unsubstituted aryl. Alternatively, $R^1$ is unsubstituted phenyl.

$R^2$ may be selected from hydrogen, —CN, —OH, unsubstituted C$_1$-C$_{20}$ alkyl, and unsubstituted 2 to 20 membered heteroalkyl. $R^2$ may be selected from hydrogen, —CN, —OH, unsubstituted C$_1$-C$_8$ alkyl, and unsubstituted 2 to 8 membered heteroalkyl.

$R^3$ may be selected from unsubstituted C$_5$-C$_7$ cycloalkyl, unsubstituted 5 to 7 membered heterocycloalkyl, unsubstituted aryl, unsubstituted heteroaryl, C$_5$-C$_7$ cycloalkyl substituted with a lower substituent, 5 to 7 membered heterocycloalkyl substituted with a lower substituent, aryl substituted with a lower substituent, and heteroaryl substituted with a lower substituent. $R^3$ may also be selected from a C$_1$-C$_5$ alkyl an a 2 to 5 membered heteroalkyl; both substituted with a substituent selected from an unsubstituted aryl, and an aryl substituted with a lower substituent. Alternatively, $R^3$ is selected from unsubstituted benzyl and benzyl substituted with a lower substituent.

$R^4$ may be selected from hydrogen, unsubstituted $C_1$-$C_5$ alkyl, and $C_1$-$C_5$ alkyl substituted with a lower substituent. $R^4$ may also be selected from hydrogen, and unsubstituted $C_1$-$C_5$ alkyl. In some embodiments, $R^4$ is hydrogen.

In an exemplary embodiment, $L^1$ is selected from a bond, —O—, —S—, —SO$_2$—, —C(O)N—, —C(O)O—, —C(O)—, unsubstituted $C_1$-$C_{20}$ alkylene, and unsubstituted 2 to 20 membered heteroalkylene.

In another embodiment, the compound of the present invention has the formula

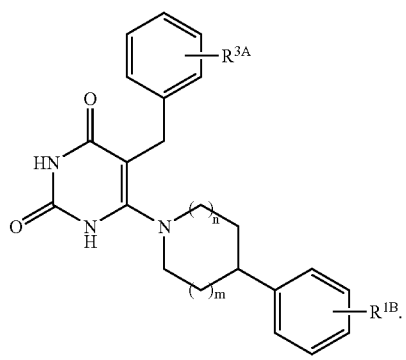

(II)

In Formula (II), $R^{3A}$ and $R^{1B}$ are independently selected from halogen, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —CN, —CF$_3$, —OR$^5$, —SR$^6$, —NR$^7$R$^8$, -L$^3$—C(O)R$^9$, and -L$^4$—S(O)$_2$R$^{10}$. $L^3$ and $L^4$ are independently selected from a bond and —NH—.

$R^5$, $R^6$, $R^7$, and $R^8$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^7$ and $R^8$ may be optionally joined to form a ring with the nitrogen to which they are attached.

$R^9$ and $R^{10}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, and —NR$^{11}$R$^{12}$. $R^{11}$ and $R^{12}$ are independently selected from the hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

In an exemplary embodiment, each substituted group described above in the compound of Formula (II) is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, and/or substituted heteroalkylene, described above in the compound of Formula (II) are substituted with at least one substituent group. In other embodiments, at least one or all of these groups are substituted with at least one size-limited group. Alternatively, at least one or all of these groups are substituted with at least one lower substituent group.

In other exemplary embodiments of the compound of Formula (II), each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, each substituted or unsubstituted heterocycloalkyl is a substituted or unsubstituted 4 to 8 membered heterocycloalkyl, each substituted or unsubstituted alkylene is a substituted or unsubstituted $C_1$-$C_{20}$ alkylene, and/or each substituted or unsubstituted heteroalkylene is a substituted or unsubstituted 2 to 20 membered heteroalkylene.

Alternatively, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, each substituted or unsubstituted heterocycloalkyl is a substituted or unsubstituted 5 to 7 membered heterocycloalkyl, each substituted or unsubstituted alkylene is a substituted or unsubstituted $C_1$-$C_8$ alkylene, and/or each substituted or unsubstituted heteroalkylene is a substituted or unsubstituted 2 to 8 membered heteroalkylene.

II. Exemplary Syntheses

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

Scheme I

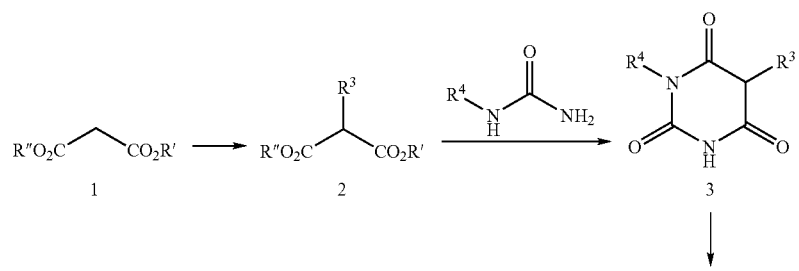

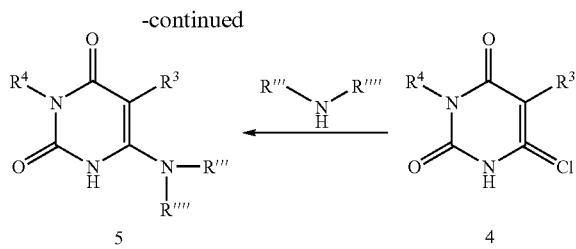

In Scheme I, $L^1$, $R^1$, $R^2$, $R^3$, and $R^4$ are as defined above in the discussion of the compounds of the present invention. R', and R" are independently methyl or ethyl. R'" and R"" are independently substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or may be joined with the nitrogen to which they are attached to form a substituted or unsubstituted ring (e.g. substituted or unsubstituted piperidinyl or substituted or unsubstituted piperizinyl).

Compound 2 may be prepared from compound 1 (Scheme I) by alkylation with a suitable alkylating agent (such as an alkyl halide or benzyl halide) in the presence of a base (e.g. sodium hydride in a non-protic solvent, such as THF), at a temperature between 0° C. and the boiling point of the solvent. Alternatively, when $R^3$ is an aryl group, compound 2 may be prepared through a palladium-catalyzed coupling reaction of the appropriate aryl halides with a malonate ester (Beare, N. A.; Hartwig, J. F. *J. Org. Chem.* 2002, 67, 541-555). Additionally, compound 2 is well-known and may be prepared from a variety of methods familiar to those skilled in the art.

Compound 3 may be prepared from compounds 2 by treatment with a suitably monosubstituted urea. The reaction is generally conducted in a polar solvent (e.g. an alcohol, such as methanol, ethanol, isopropanol, or dimethylformamide) and optionally in the presence of a base (e.g. a metal alkoxide, such as sodium methoxide). The reaction is generally carried out at a temperature between ambient temperature and the reflux temperature of the solvent, preferably at the reflux temperature.

Compound 4 may be prepared from compound 3 by treatment with a suitable chlorinating agent (e.g. a phosphorus or sulphur halide in a suitable oxidation state such as thionyl chloride, phosphorous pentachloride, or preferably phosphorous oxychloride). When the reaction is carried out with phosphorus oxychloride, the addition of phosphoric acid ($H_3PO_4$) or benzyltriethylammonium chloride (BTEAC) may be beneficial.

Compound 5 may be prepared from compound 4 by treatment with a suitably substituted amine. The reaction is carried out in the presence of a solvent such as dimethylformamide, or an alcohol (e.g. 1-butanol), in the presence of a base (e.g. sodium acetate or a tertiary amine base, such as diisopropylethylamine). The reaction is generally carried out at the reflux temperature of the solvent. Additionally, the reaction can be carried out under microwave conditions in a sealed vessel, in which case the reaction may be performed at temperatures higher than the boiling point of the solvent at atmospheric pressure (for example, 160° C. for 1-butanol and 200° C. in the case of dimethylformamide). The amines NH(R'")(R"") are generally known compounds and may be prepared from compounds according to known methods familiar to those skilled in the art.

Scheme II

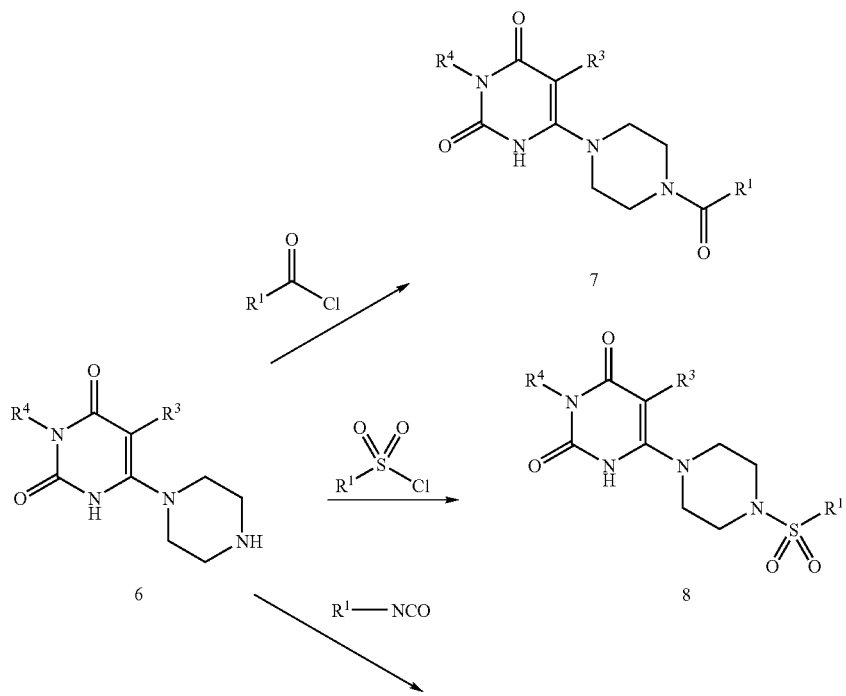

-continued

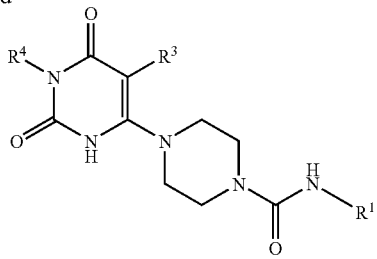

9

In Scheme II, R¹, R³, and R⁴ are as defined above in the discussion of the compounds of the present invention.

Compounds 7, 8 and 9 may be prepared from compound 6 by reaction with a suitable electrophile (Scheme II). Thus, reaction of compound 6 with an acid chloride, optionally in the presence of a base (e.g. diisopropylethylamine) in an inert solvent (e.g. dichloromethane), yields amide 7. In a similar fashion, treatment of compound 6 with a sulfonyl halide (e.g. sulfonyl chloride) optionally in the presence of a base (e.g. a tertiary amine such as diisopropylethylamine), in an inert solvent such as dichloromethane, yields sulfonamide 8. The reaction of compound 6 with an isocyanate in a suitable solvent inert to the reagents, provides the urea of formula 9.

III. Assays and Methods for Modulating Glucocorticoid Receptor Activity

The compounds of the present invention can be tested for their antiglucocorticoid properties. Methods of assaying compounds capable of modulating glucocorticoid receptor activity are presented herein. Typically, compounds of the current invention are capable of modulating glucocorticoid receptor activity by selectively binding to the GR or by preventing GR ligands from binding to the GR. In some embodiments, the compounds exhibit little or no cytotoxic effect. Therefore, exemplary assays disclosed herein may test the ability of compounds to (1) tightly bind to the GR; (2) selectively bind to the GR; (3) prevent GR ligands from binding to the GR; (4) modulate the activity of the GR in a cellular system; and/or (5) exhibit non-cytotoxic effects.

A. Binding Assays

In some embodiments, GR modulators are identified by screening for molecules that compete with a ligand of GR, such as dexamethasone. Those of skill in the art will recognize that there are a number of ways to perform competitive binding assays. In some embodiments, GR is pre-incubated with a labeled GR ligand and then contacted with a test compound. This type of competitive binding assay may also be referred to herein as a binding displacement assay. Alteration (e.g., a decrease) of the quantity of ligand bound to GR indicates that the molecule is a potential GR modulator. Alternatively, the binding of a test compound to GR can be measured directly with a labeled test compound. This latter type of assay is called a direct binding assay.

Both direct binding assays and competitive binding assays can be used in a variety of different formats. The formats may be similar to those used in immunoassays and receptor binding assays. For a description of different formats for binding assays, including competitive binding assays and direct binding assays, see *Basic and Clinical Immunology* 7th Edition (D. Stites and A. Terr ed.) 1991; *Enzyme Immunoassay*, E. T. Maggio, ed., CRC Press, Boca Raton, Fla. (1980); and "Practice and Theory of Enzyme Immunoassays," P. Tijssen, *Laboratory Techniques in Biochemistry and Molecular Biology*, Elsevier Science Publishers B. V. Amsterdam (1985), each of which is incorporated herein by reference.

In solid phase competitive binding assays, for example, the sample compound can compete with a labeled analyte for specific binding sites on a binding agent bound to a solid surface. In this type of format, the labeled analyte can be a GR ligand and the binding agent can be GR bound to a solid phase. Alternatively, the labeled analyte can be labeled GR and the binding agent can be a solid phase GR ligand. The concentration of labeled analyte bound to the capture agent is inversely proportional to the ability of a test compound to compete in the binding assay.

Alternatively, the competitive binding assay may be conducted in liquid phase, and any of a variety of techniques known in the art may be used to separate the bound labeled protein from the unbound labeled protein. For example, several procedures have been developed for distinguishing between bound ligand and excess bound ligand or between bound test compound and the excess unbound test compound. These include identification of the bound complex by sedimentation in sucrose gradients, gel electrophoresis, or gel isoelectric focusing; precipitation of the receptor-ligand complex with protamine sulfate or adsorption on hydroxylapatite; and the removal of unbound compounds or ligands by adsorption on dextran-coated charcoal (DCC) or binding to immobilized antibody. Following separation, the amount of bound ligand or test compound is determined.

Alternatively, a homogenous binding assay may be performed in which a separation step is not needed. For example, a label on the GR may be altered by the binding of the GR to its ligand or test compound. This alteration in the labeled GR results in a decrease or increase in the signal emitted by label, so that measurement of the label at the end of the binding assay allows for detection or quantitation of the GR in the bound state. A wide variety of labels may be used. The component may be labeled by any one of several methods. Useful radioactive labels include those incorporating $^3$H, $^{125}$I, $^{35}$S, $^{14}$C, or $^{32}$P. Useful non-radioactive labels include those incorporating fluorophores, chemiluminescent agents, phosphorescent agents, electrochemiluminescent agents, and the like. Fluorescent agents are especially useful in analytical techniques that are used to detect shifts in protein structure such as fluorescence anisotropy and/or fluorescence polarization. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference in its entirety for all purposes. The label may be coupled directly or indirectly to the desired component of the assay according to methods well known in the art.

For competitive binding assays, the amount of inhibition may be determined using the techniques disclosed herein. The amount of inhibition of ligand binding by a test compound depends on the assay conditions and on the concentrations of ligand, labeled analyte, and test compound that are used. In an exemplary embodiment, a compound is said to be capable of inhibiting the binding of a GR ligand to a GR in a competitive binding assay if the inhibition constant ($K_i$) is less than 5 µM using the assay conditions presented in Example 5. In another exemplary embodiment, a compound is said to be capable of inhibiting the binding of a GR ligand to a GR in a competitive binding assay if the $K_i$ is less than 1 µM using the assay conditions presented in Example 5. In another exemplary embodiment, a compound is said to be capable of inhibiting the binding of a GR ligand to a GR in a competitive binding assay if the $K_i$ is less than 100 nM using the assay conditions presented in Example 5. In another exemplary embodiment, a compound is said to be capable of inhibiting the binding of a GR ligand to a GR in a competitive binding assay if the $K_i$ is less than 10 nM using the assay conditions presented in Example 5. In another exemplary embodiment, a compound is said to be capable of inhibiting the binding of a GR ligand to a GR in a competitive binding assay if the $K_i$ is less than 1 nM using the assay conditions presented in Example 5. In another exemplary embodiment, a compound is said to be capable of inhibiting the binding of a GR ligand to a GR in a competitive binding assay if the $K_i$ is less than 100 pM using the assay conditions presented in Example 5. In another exemplary embodiment, a compound is said to be capable of inhibiting the binding of a GR ligand to a GR in a competitive binding assay if the $K_i$ is less than 10 pM using the assay conditions presented in Example 5.

High-throughput screening methods may be used to assay a large number of potential modulator compounds. Such "compound libraries" are then screened in one or more assays, as described herein, to identify those library members (particular chemical species or subclasses) that display a desired characteristic activity. Preparation and screening of chemical libraries is well known to those of skill in the art. Devices for the preparation of chemical libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

B. Cell-Based Assays

Cell-based assays involve whole cells or cell fractions containing GR to assay for binding or modulation of activity of GR by a compound of the present invention. Exemplary cell types that can be used according to the methods of the invention include, e.g., any mammalian cells including leukocytes such as neutrophils, monocytes, macrophages, eosinophils, basophils, mast cells, and lymphocytes, such as T cells and B cells, leukemias, Burkitt's lymphomas, tumor cells (including mouse mammary tumor virus cells), endothelial cells, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, GR can be expressed in cells that do not express an endogenous version of GR.

In some cases, fragments of GR, as well as protein fusions, can be used for screening. When molecules that compete for binding with GR ligands are desired, the GR fragments used are fragments capable of binding the ligands (e.g., dexamethasone). Alternatively, any fragment of GR can be used as a target to identify molecules that bind GR. GR fragments can include any fragment of, e.g., at least 20, 30, 40, 50 amino acids up to a protein containing all but one amino acid of GR. Typically, ligand-binding fragments will comprise transmembrane regions and/or most or all of the extracellular domains of GR.

In some embodiments, signaling triggered by GR activation is used to identify GR modulators. Signaling activity of GR can be determined in many ways. For example, downstream molecular events can be monitored to determine signaling activity. Downstream events include those activities or manifestations that occur as a result of stimulation of a GR receptor. Exemplary downstream events useful in the functional evaluation of transcriptional activation and antagonism in unaltered cells include upregulation of a number of glucocorticoid response element (GRE)-dependent genes (PEPCK, tyrosine amino transferase, aromatase). In addition, specific cell types susceptible to GR activation may be used, such as osteocalcin expression in osteoblasts which is downregulated by glucocorticoids; primary hepatocytes which exhibit glucocorticoid mediated upregulation of PEPCK and glucose-6-phospahte (G-6-Pase)). GRE-mediated gene expression has also been demonstrated in transfected cell lines using well-known GRE-regulated sequences (e.g. the mouse mammary tumor virus promoter (MMTV) transfected upstream of a reporter gene construct). Examples of useful reporter gene constructs include luciferase (luc), alkaline phosphatase (ALP) and chloramphenicol acetyl transferase (CAT). The functional evaluation of transcriptional repression can be carried out in cell lines such as monocytes or human skin fibroblasts. Useful functional assays include those that measure IL-1beta stimulated IL-6 expression; the downregulation of collagenase, cyclooxygenase-2 and various chemokines (MCP-1, RANTES); or expression of genes regulated by NFkB or AP-1 transcription factors in transfected cell-lines. An example of a cell-based assay measuring gene transcription is presented in Example 6.

Typically, compounds that are tested in whole-cell assays are also tested in a cytotoxicity assay. Cytotoxicity assays are used to determine the extent to which a perceived modulating effect is due to non-GR binding cellular effects. In an exemplary embodiment, the cytotoxicity assay includes contacting a constitutively active cell with the test compound. Any decrease in cellular activity indicates a cytotoxic effect. An exemplary cytotoxicity assay is presented in Example 8.

C. Specificity

The compounds of the present invention may be subject to a specificity assay (also referred to herein as a selectivity assay). Typically, specificity assays include testing a compound that binds GR in vitro or in a cell-based assay for the degree of binding to non-GR proteins. Selectivity assays may be performed in vitro or in cell based systems, as described above. GR binding may be tested against any appropriate non-GR protein, including antibodies, receptors, enzymes, and the like. In an exemplary embodiment, the non-GR binding protein is a cell-surface receptor or nuclear receptor. In another exemplary embodiment, the non-GR protein is a steroid receptor, such as estrogen receptor, progesterone receptor, androgen receptor, or mineralocorticoid receptor. An exemplary specificity assay is presented in Example 7.

D. Methods of Modulating GR Activity

In another aspect, the present invention provides methods of modulating glucocorticoid receptor activity using the techniques described above. In an exemplary embodiment, the method includes contacting a GR with a compound of the present invention, such as the compound of Formula (I), and detecting a change in GR activity.

In an exemplary embodiment, the GR modulator is an antagonist of GR activity (also referred to herein as "a glucocorticoid receptor antagonist"). A glucocorticoid receptor antagonist, as used herein, refers to any composition or compound which partially or completely inhibits (antagonizes) the binding of a glucocorticoid receptor (GR) agonist (e.g. cortisol and synthetic or natural cortisol analog) to a GR thereby inhibiting any biological response associated with the binding of a GR to the agonist.

In a related embodiment, the GR modulator is a specific glucocorticoid receptor antagonist. As used herein, a specific glucocorticoid receptor antagonist refers to any composition or compound which inhibits any biological response associated with the binding of a GR to an agonist by preferentially binding to the GR rather than another nuclear receptor (NR). In some embodiments, the specific glucocorticoid receptor antagonist binds preferentially to GR rather than the mineralocorticoid receptor (MR) or progesterone receptor (PR). In an exemplary embodiment, the specific glucocorticoid receptor antagonist binds preferentially to GR rather than the mineralocorticoid receptor (MR). In another exemplary embodiment, the specific glucocorticoid receptor antagonist binds preferentially to GR rather than the progesterone receptor (PR).

In a related embodiment, the specific glucocorticoid receptor antagonist binds to the GR with an association constant ($K_d$) that is at least 10-fold less than the $K_d$ for the NR. In another embodiment, the specific glucocorticoid receptor antagonist binds to the GR with an association constant ($K_d$) that is at least 100-fold less than the $K_d$ for the NR. In another embodiment, the specific glucocorticoid receptor antagonist binds to the GR with an association constant ($K_d$) that is at least 1000-fold less than the $K_d$ for the NR.

In an exemplary embodiment, the present invention provides a method of treating a disorder or condition. The method includes modulating a glucocorticoid receptor by administering to a subject in need of such treatment, an effective amount of a compound of the present invention.

Methods of treating a disorder or condition through antagonizing a glucocorticoid receptor are also provided. The method includes administering to a subject in need of such treatment, an effective amount of a compound of the present invention.

In other embodiments, a method of modulating a glucocorticoid receptor is provided. The method includes the steps of contacting a glucocorticoid receptor with a compound of the present invention and detecting a change in the activity of the glucocorticoid receptor.

IV. Pharmaceutical Compositions of Glucocorticoid Receptor Modulators

In another aspect, the present invention provides pharmaceutical compositions. The pharmaceutical composition includes a pharmaceutically acceptable excipient and a compound of having the formula:

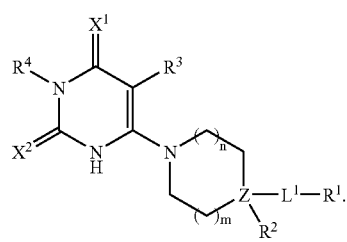

(I)

Where a pharmaceutical composition includes a compound of Formula (I), n, m, Z, $X^1$, $X^2$, $L^1$, $R^1$, $R^2$, and $R^4$ are as defined above in the discussion of the compounds of the present invention. $R^3$ is also as defined above, with the exception that $R^3$ is selected from substituted or unsubstituted arylalkyl, substituted or unsubstituted heteroarylalkyl, substituted or unsubstituted cycloalkyl-alkyl, substituted or unsubstituted heterocycloalkyl-alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the pharmaceutical composition includes a pharmaceutically acceptable excipient and a compound of having the formula:

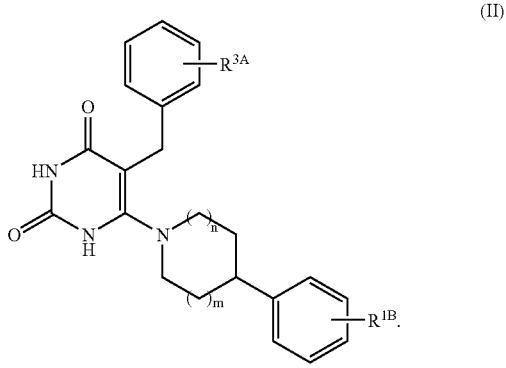

(II)

In Formula (II), n, m, $R^{3A}$, and $R^{1B}$ is as defined above in the discussion of the compounds of the present invention.

The pharmaceutical compositions described herein are typically used to treat a disorder or condition through modulating a glucocorticoid receptor in a subject in need of such treatment.

In an exemplary embodiment, the pharmaceutical composition includes from 1 to 2000 milligrams of the compound of Formula (I) or (II). In some embodiments, the pharmaceutical composition includes from 1 to 1500 milligrams of the compound of Formulae or (II). In other embodiments, the pharmaceutical composition includes from 1 to 1000 milligrams of the compound of Formulae (I) or (II).

The compounds of the present invention can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The GR modulators of this invention can also be administered by in intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Thus, the pharmaceutical compositions described herein may be adapted for oral administration. In some embodiments, the pharmaceutical composition is in the form of a tablet. Moreover, the present invention provides pharmaceutical compositions including a pharmaceutically acceptable carrier or excipient and either a compound of Formulae (I) or (II), or a pharmaceutically acceptable salt of a compound of Formulae (I) or (II).

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethyl-cellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR modulator mixed with a filler or binders such as lactose or starches, lubricants such as talc or magnesium stearate, and, optionally, stabilizers. In soft capsules, the GR modulator compounds may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a GR modulator in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The GR modulators of the invention can be delivered by transdermally, by a topical route, formulated as applicator sticks, solutions, suspensions, emulsions, gels, creams, ointments, pastes, jellies, paints, powders, and aerosols.

The GR modulators of the invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The GR modulator pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use In another embodiment, the GR modulator formulations of the invention are useful for parenteral administration, such as intravenous (IV) administration or administration into a body cavity or lumen of an organ. The formulations for administration will commonly comprise a solution of the GR modulator dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of GR modulator in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the GR modulator formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR modulator into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

V. Methods for Treating Conditions Mediated by Glucocorticoid Receptors

In still another aspect, the present invention provides a method for the treatment of a disorder or condition through modulation of a glucocorticoid receptor. In this method, a subject in need of such treatment is administered an effective amount of a compound having one of the formulae provided above. The amount is effective in modulating the glucocorticoid receptor.

A variety of disease sates are capable of being treated with glucocorticoid receptor modulators. Exemplary disease states include major psychotic depression, mild cognitive impairment, psychosis, dementia, hyperglycemia, stress disorders, antipsychotic induced weight gain, delirium, cognitive impairment in depressed patients, cognitive deterioration in individuals with Down's syndrome, psychosis associated with interferon-alpha therapy, chronic pain (e.g. pain associate with gastroesophageal reflux disease), postpartum psychosis, postpartum depression, neurological disorders in premature infants, migraine headaches, obesity, diabetes, cardiovascular disease, hypertension, Syndrome X, depression, anxiety, glaucoma, human immunodeficiency virus (HIV) or acquired immunodeficiency syndrome (AIDS), neurodegeneration (e.g. Alzheimer's disease and Parkinson's disease), cognition enhancement, Cushing's Syndrome, Addison's Disease, osteoperosis, frailty, inflammatory diseases (e.g., osteoarthritis, rheumatoid arthritis, asthma and rhinitis), adrenal function-related ailments, viral infection, immunodeficiency, immunomodulation, autoimmune diseases, allergies, wound healing, compulsive behavior, multidrug resistance, addiction, psychosis, anorexia, cahexia, posttraumatic stress syndrome post-surgical bone fracture, medical catabolism, and muscle frailty. The methods of treatment includes administering to a patient in need of such treatment, a therapeutically effective amount of a compound according to Formulae (I) or (II), or a pharmaceutically acceptable salt thereof.

Thus, in an exemplary embodiment, the present invention provides a method of treating a disorder or condition through modulating a GR, the method including administering to a subject in need of such treatment, an effective amount of a compound of the present invention, such as a compound of Formulae (I) or (II).

The amount of GR modulator adequate to treat a disease through modulating the GR is defined as a "therapeutically effective dose". The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, GR modulator and disease or condition treated.

Single or multiple administrations of GR modulator formulations can be administered depending on the dosage and frequency as required and tolerated by the patient. The formulations should provide a sufficient quantity of active agent to effectively treat the disease state. Thus, in one embodiment, the pharmaceutical formulations for oral administration of GR modulator is in a daily amount of between about 0.5 to about 20 mg per kilogram of body weight per day. In an alternative embodiment, dosages are from about 1 mg to about 4 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable GR modulator formulations will be known or apparent to those skilled in the art and are described in more detail in such publications as Remington's, supra. See also Nieman, In "Receptor Mediated Antisteroid Action," Agarwal, et al., eds., De Gruyter, N.Y. (1987).

After a pharmaceutical composition including a GR modulator of the invention has been formulated in an acceptable carrier, it can be placed in an appropriate container and labeled for treatment of an indicated condition. For administration of GR modulators, such labeling would include, e.g., instructions concerning the amount, frequency and method of administration. In one embodiment, the invention provides for a kit for the treatment of delirium in a human which includes a GR modulator and instructional material teaching the indications, dosage and schedule of administration of the GR modulator.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, the features of the GR modulator compounds are equally applicable to the methods of treating disease states described herein. All publications, patents, and patent applications cited herein are hereby incorporated by reference in their entirety for all purposes.

VI. EXAMPLES

The following examples are provided solely to illustrate the present invention and are not intended to limit the scope of the invention, as described herein.

High Pressure Liquid Chromatography—Mass Spectrometry (LCMS) experiments to determine retention times (RT) and associated mass ions were performed using one of the following methods. Solvent A is water and solvent B is acetonitrile.

Method A: Experiments performed on a Micromass Platform LC spectrometer with positive and negative ion electrospray and ELS/Diode array detection using a Phenomenex Luna C18(2) 30×4.6 mm column and a 2 mL/minute flow rate. The solvent system was 95% solvent A and 5% solvent B for the first 0.50 minutes followed by a gradient up to 5% solvent A and 95% solvent B over the next 4 minutes. The final solvent system was held constant for a further 0.50 minutes.

Method B: Experiments performed on a Micromass Platform LCT spectrometer with positive ion electrospray and single wavelength UV 254 nm detection using a Higgins Clipeus C18 5 μm 100×3.0 mm column and a 2 mL/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 2 minutes.

Example 1

2-(3-Chlorobenzyl)malonic acid diethyl ester
(Compound 2; R' and R"=Et, $R^3$=3-chlorobenzyl)

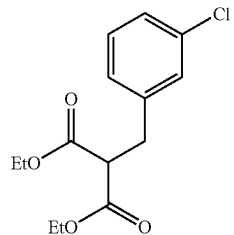

To a suspension of sodium hydride 95.24 g, 0.131 mmol of a 60% dispersion in mineral oil) in THF at 0° C. was added diethyl malonate (20.0 g; 0.125 mmol) dropwise. The contents were warmed to ambient temperature and 3-chlorobenzyl chloride (21.1 g, 0.131 mmol) added. The contents were heated to reflux for 18 hrs, cooled and concentrated in vacuo. The solid residue thus obtained was dissolved in water and extracted with diethyl ether, the organics washed with brine, dried (MgSO$_4$) and concentrated to give a colourless oil. Flash column chromatography on silica gel with 5% diethyl ether in cyclohexane gave the product as a colourless oil, 20.0 g. LC-MS: 3.78 mins, 285 (M+H)$^+$.

Also prepared by this method were the following compounds:

2-Phenethylmalonic acid diethyl ester (Compound 2; R' and R"=Et, $R^3$=phenethyl)

2-Pyridin-4-ylmethylmalonic acid diethyl ester (Compound 2; R' and R"=Et, $R^3$=4-pyridylmethyl)

2-(3-Methoxybenzyl)malonic acid diethyl ester (Compound 2; R' and R"=Et, $R^3$=3-methoxybenzyl)

2-(3-Bromobenzyl)malonic acid diethyl ester (Compound 2; R' and R"=Et, $R^3$=3-bromobenzyl)

2-(4-Chlorobenzyl)malonic acid diethyl ester (Compound 2; R' and R"=Et, $R^3$=4-chlorobenzyl)

2-(2-Chlorobenzyl)malonic acid diethyl ester (Compound 2; R' and R"=Et, $R^3$=2-chlorobenzyl)

2-(3-Cyanobenzyl)malonic acid diethyl ester (Compound 2; R' and R"=Et, $R^3$=3-cyanobenzyl)

2-(4-Cyanobenzyl)malonic acid diethyl ester (Compound 2; R' and R"=Et, $R^3$=4-cyanobenzyl)

2-(2-Cyanobenzyl)malonic acid diethyl ester (Compound 2; R' and R"=Et, $R^3$=2-cyanobenzyl)

2-(3-Methoxybenzyl)malonic acid diethyl ester (Compound 2; R' and R"=Et, $R^3$=3-methoxybenzyl)

2-(3-Nitrobenzyl)malonic acid diethyl ester (Compound 2; R' and R"=Et, $R^3$=3-nitrobenzyl)

2-(2-Nitrobenzyl)malonic acid diethyl ester (Compound 2; R' and R"=Et, $R^3$=2-nitrobenzyl)

2-(4-Nitrobenzyl)malonic acid diethyl ester (Compound 2; R' and R"=Et, $R^3$=4-nitrobenzyl)

2-(4-Methoxybenzyl)malonic acid diethyl ester (Compound 2; R' and R"=Et, $R^3$=4-methoxybenzyl)

2-(2-Methoxybenzyl)malonic acid diethyl ester (Compound 2; R' and R"=Et, $R^3$=2-methoxybenzyl).

Example 2

5-(3-Chlorobenzyl)-1-methylpyrimidin-2,4,6-trione (Compound 3; $R^3$=3-chlorobenzyl, $R^4$=methyl)

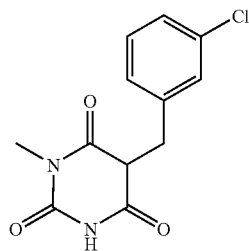

Methylurea (1.18 g, 16.0 mmol) and freshly prepared sodium methoxide (1.04 g, 19.2 mmol) were combined in dimethylformamide (15 mL) and a solution of 2-(3-chlorobenzyl)malonic acid diethyl ester (2.85 g, 10.0 mmol) in dimethylformamide (5 mL) was added. The reaction temperature was raised to 130° C. for 2 hours and then cooled to ambient temperature before water was added and the solution acidified with 2N HCl$_{aq}$. The resulting solid was filtered then washed with water and the dried to afford the product as a white solid, 840 mg. LC-MS: RT=2.87 mins, 267 (M+H)$^+$ 265 (M–H)$^-$.

Also prepared by this method were the following compounds:

1-Methyl-5-phenethylpyrimidine-2,4,6-trione (Compound 3, $R^3$=phenethyl, $R^4$=methyl). LC-MS: RT=2.82 mins 247 (M+H)$^+$, 245 (M–H)$^-$ 5-Isobutyl-l-methylpyrimidine-2,4,6-trione (Compound 3, $R^3$=isobutyl, $R^4$=methyl). LC-MS: RT=2.44 mins 199 (M+H)$^+$, 197 (M–H)$^-$ 1-Benzyl-5-(3-chlorobenzyl)pyrimidine-2,4,6-trione (Compound 3, $R^3$=3-chlorobenzyl, $R^4$=benzyl). LC-MS: RT=3.61 mins 341 (M–H)$^-$ 5-(3-Chlorobenzyl)-1-isobutylpyrimidine-2,4,6-trione (Compound 3, $R^3$=3-chlorobenzyl, $R^4$=isobutyl). LC-MS: RT=3.55 mins 307 (M–H)$^-$ 5-(3-Chlorobenzyl)-1-phenylpyrimidine-2,4,6-trione (Compound 3, $R^3$=3-chlorobenzyl, $R^4$=phenyl). LC-MS: RT=3.30 mins 327 (M–H)$^-$, 329 (M+H)$^+$ 5-Benzylpyrimidine-2,4,6-trione (Compound 3, $R^3$=H, $R^4$=H). LC-MS: RT=1.99 mins 219 (M+H)$^+$ 5-(3-Chlorobenzyl)-1-ethylpyrimidine-2,4,6-trione (Compound 3, $R^3$=3-chlorobenzyl, $R^4$=ethyl). $^1$H NMR (D6-DMSO) 7.56-7.02 (4H, m, aromatic C$\underline{H}$), 4.11 (2H, q, C$\underline{H}_H$—CH$_3$), 4.04 (1H, t, C$\underline{H}$—CH$_2$), 3.19 (2H, d, C$\underline{H}_2$—CH), 1.45 (3H, t, CH$_2$—C$\underline{H}_3$).

5-(3-Chlorobenzyl)-1-phenylpyrimidine-2,4,6-trione (Compound 3, $R^3$=3-chlorobenzyl, $R^4$=phenyl). LC-MS: RT=3.30 mins 327 (M–H)$^-$, 329 (M+H)$^+$ 5-(2-Chlorobenzyl)-1-methylpyrimidine-2,4,6-trione (Compound 3, $R^3$=2-chlorobenzyl, $R^4$=methyl). $^1$H NMR (D6-DMSO) 7.48-6.87 (4H, m, aromatic C$\underline{H}$), 4.09 (1H, t, C$\underline{H}$—CH$_2$), 3.26 (2H, d, C$\underline{H}_2$—CH), 3.05 (3H, s, N—C$\underline{H}_3$).

5-(2-Chlorobenzyl)pyrimidine-2,4,6-trione (Compound 3, $R^3$=2-chlorobenzyl, $R^4$=H). $^1$H NMR (D6-DMSO) 7.52-6.94 (4H, m, aromatic C$\underline{H}$), 4.06 (1H, t, C$\underline{H}$—CH$_2$), 3.25 (2H, d, C$\underline{H}_2$—CH).

5-(3-Chlorobenzyl)pyrimidine-2,4,6-trione (Compound 3, $R^3$=3-chlorobenzyl, $R^4$=H). $^1$H NMR (CDCl$_3$) 7.31-7.08 (4H, m, aromatic C$\underline{H}$), 3.71 (1H, t, C$\underline{H}$—CH$_2$), 3.48 (2H, d, CH$_2$—CH).

5-(4-Chlorobenzyl)pyrimidine-2,4,6-trione (Compound 3, $R^3$=4-chlorobenzyl, $R^4$=H). LC-MS: RT=2.48 mins 251 (M–H)$^-$ 5-(3-Bromobenzyl)pyrimidine-2,4,6-trione (Compound 3, $R^3$=3-bromobenzyl, $R^4$=H). LC-MS: RT=2.51 mins 297 (M+H)$^+$ 5-(3-Methoxybenzyl)pyrimidine-2,4,6-trione (Compound 3, $R^3$=3-methoxybenzyl, $R^4$=H). LC-MS: RT=2.17 mins 249 (M+H)$^+$, 247 (M–H)$^-$ 5-Benzyl-1-methylpyrimidine-2,4,6-trione (Compound 3, $R^3$=benzyl, $R^4$=methyl). LC-MS: RT=2.51 mins, 231 (M–H)$^-$ 5-(3-Cyanobenzyl)pyrimidine-2,4,6-trione (Compound 3, $R^3$=3-cyanobenzyl, $R^4$=H). LC-MS: RT=2.26 mins, 242 (M–H)$^-$ 5-(3-Nitrobenzyl)pyrimidine-2,4,6-trione (Compound 3, $R^3$=3-nitrobenzyl, $R^4$=H). LC-MS: RT=2.42 mins, 262 (M–H)$^-$ 5-(4-Methoxybenzyl)pyrimidine-2,4,6-trione (Compound 3, $R^3$=4-methoxybenzyl, $R^4$=H). LC-MS: RT=2.26 mins, no molecular ion seen.

5-(2-Methoxybenzyl)pyrimidine-2,4,6-trione (Compound 3, $R^3$=2-methoxybenzyl, $R^4$=H). LC-MS: RT=2.42 mins, no molecular ion seen.

Example 3

6-Chloro-5-(3-chlorobenzyl)-3-methyl-1H-pyrimidine-2,4-dione. (Compound 4, $R^3$=3-chlorobenzyl, $R^4$=methyl)

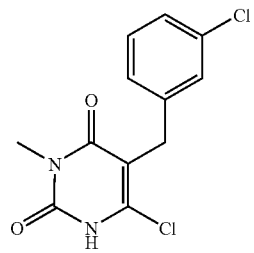

5-(3-Chlorobenzyl)-1-methylpyrimidin-2,4,6-trione (760 mg, 2.85 mmol) was dissolved in POCl$_3$ and to it was added benzyltriethylammonium chloride (5.70 mmol) at 0° C. After 10 mins the reaction was warmed to ambient temperature and then heated at 70° C. for 2 hrs. The contents were cooled in an ice bath and water carefully added. The precipitate that formed was removed by filtration, washed with water and dried to give the product as a yellow solid, 160 mg. LC-MS: RT=3.14 mins 283 (M–H)⁻

Also prepared by this method were the following compounds:

6-Chloro-3-methyl-5-phenyl-1H-pyimidine-2,4-dione. (Compound 4, $R^3$=phenyl, $R^4$=methyl). LC-MS: RT=2.55 mins 235 (M–H)⁻

6-Chloro-3-methyl-5-phenethyl-1H-pyimidine-2,4-dione. (Compound 4, $R^3$=phenethyl, $R^4$=methyl). LC-MS: RT=3.05 mins 263 (M–H)⁻

3-Benzyl-6-chloro-5-(3-chlorobenzyl)-1H-pyimidine-2,4-dione. (Compound 4, $R^3$=3-chlorobenzyl, $R^4$=benzyl). LC-MS: RT=3.79 mins 359 (M–H)⁻

6-Chloro-5-isobutyl-3-methyl-1H-pyrimidine-2,4-dione. (Compound 4, $R^3$=isobutyl, $R^4$=methyl). LC-MS: RT=2.76 mins 215 (M–H)⁻

6-Chloro-5-(3-chlorobenzyl)-3-phenyl-1H-pyrimidine-2,4-dione. (Compound 4, $R^3$=3-chlorobenzyl, $R^4$=phenyl). LC-MS: RT=3.44 mins 345 (M–H)⁻

6-Chloro-5-(3-chlorobenzyl)-3-isobutyl-1H-pyrimidine-2,4-dione. (Compound 4, $R^3$=3-chlorobenzyl, $R^4$=isobutyl). LC-MS: RT=3.73 mins 325 (M–H)⁻

6-Chloro-5-(3-chlorobenzyl)-3-ethyl-1H-pyrimidine-2,4-dione. (Compound 4, $R^3$=3-chlorobenzyl, $R^4$=ethyl). LC-MS: RT=3.35 mins 297 (M–H)⁻

6-Chloro-5-(2-chlorobenzyl)-1H-pyrimidine-2,4-dione. (Compound 4, $R^3$=2-chlorobenzyl, $R^4$=H). LC-MS: RT=2.76 mins 269 (M–H)⁻

6-Chloro-5-(2-chlorobenzyl)-3-methyl-1H-pyrimidine-2,4-dione. (Compound 4, $R^3$=2-chlorobenzyl, $R^4$=methyl). LC-MS: RT=3.08 mins 283 (M–H)⁻

6-Chloro-5-(3-chlorobenzyl)-1H-pyrimidine-2,4-dione. (Compound 4, $R^3$=3-chlorobenzyl, $R^4$=H). LC-MS: RT=2.80 mins 269 (M–H)⁻

6-Chloro-5-(4-chlorobenzyl)-1H-pyrimidine-2,4-dione. (Compound 4, $R^3$=4-chlorobenzyl, $R^4$=H). LC-MS: RT=2.83 mins 269 (M–H)⁻

5-(3-Bromobenzyl)-6-Chloro-1H-pyrimidine-2,4-dione. (Compound 4, $R^3$=3-bromobenzyl, $R^4$=H). LC-MS: RT=2.83 mins 269 (M–H)⁻

5-Benzyl-6-Chloro-1H-pyrimidine-2,4-dione. (Compound 4, $R^3$=benzyl, $R^4$=H). LC-MS: RT=2.56 mins 237 (M+H)⁺, 235 (M–H)⁻

5-Benzyl-6-chloro-3-methyl-1H-pyrimidine-2,4-dione. (Compound 4, $R^3$=benzyl, $R^4$=methyl). LC-MS: RT=2.83 mins 249 (M–H)⁻

5-(3-Methoxybenzyl)-6-chloro-1H-pyrimidine-2,4-dione. (Compound 4, $R^3$=3-methoxybenzyl, $R^4$=H). LC-MS RT 2.54 mins 266.8 (M–H)⁺

Example 4

5-Benzyl-6-(4-phenylpiperidin-1-yl)-1H-pyrimidine-2,4-dione. (Compound 5, $R^3$=Benzyl, $R^4$=H NR'''R''''=4-phenylpiperidin-1yl)

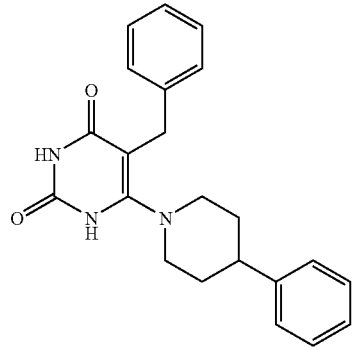

5-Benzyl-6-chloro-1H-pyimidine-2,4-dione (39 mg, 0.166 mmol), 4-phenylpiperidine (32.2 mg, 0.20 mmol) and diisopropylethylamine (35 µl, 0.20 mmol) were dissolved in DMF (0.5 mL) and microwave irradiated at 200° C. for 1 hour. The contents were cooled, diluted with water then acidified with 2N HCl and extracted with dichloromethane. The residues were purified by flash column chromatography using 2.5% MeOH in dichloromethane as eluant to give 51 mg of the title compound as a yellow oil, solidifying on standing. LC-MS: RT=3.38 mins 362 (M+H)⁺.

Also prepared by similar methods were the following compounds in Table 1 below,

TABLE 1

| $R^3$ | $R^4$ | —N(R''')(R'''') | LC-MS (RT, mass(es) found) |
|---|---|---|---|
| 3-ClBn | Bn | N-piperidinyl-phenyl | 4.38 mins 484 (M – H)⁻ |
| Bn | Me | N-piperazinyl-CH2-phenyl | 2.16 mins 391 (M + H)⁺ |
| Bn | Me | N-piperidinyl-phenyl | 3.67 mins 376 (M + H)⁺ |

TABLE 1-continued

| R³ | R⁴ | —N(R''')(R'''') | LC-MS (RT, mass(es) found) |
|---|---|---|---|
| Ph | Me | 4-benzylpiperidin-1-yl | 3.74 mins 376 (M + H)⁺ |
| Bn | H | 4-benzylpiperidin-1-yl | 3.59 mins 376 (M + H)⁺ |
| Bn | Me | 4-benzyl-4-hydroxypiperidin-1-yl | 3.22 mins 406 (M + H)⁺ |
| Bn | Me | 4-phenylpiperazin-1-yl | 3.42 mins 377 (M + H)⁺ |
| Bn | Me | 4-benzhydrylpiperazin-1-yl | 3.04 mins 467 (M + H)⁺ |
| Bn | H | 4-benzylpiperazin-1-yl | 2.02 mins 377 (M + H)⁺ |
| Bn | Me | 4-benzoylpiperidin-1-yl | 3.43 mins 404 (M + H)⁺ |
| 3-ClBn | Bn | 4-benzylpiperidin-1-yl | 4.60 mins 498 (M + H)⁺ |
| 3-ClBn | Ph | 4-benzylpiperidin-1-yl | 4.30 mins 486 (M + H)⁺ |

TABLE 1-continued
| R³ | R⁴ | —N(R''')(R'''') | LC-MS (RT, mass(es) found) |
|---|---|---|---|
| 3-ClBn | i-Bu | 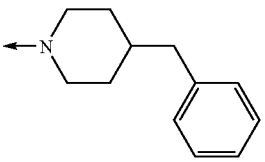 | 4.59 mins<br>466 (M + H)⁺ |
| 3-ClBn | i-Bu | 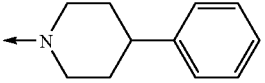 | 4.41 mins<br>438 (M + H)⁺ |
| 3-ClBn | Bn | 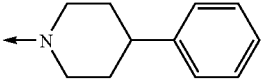 | 4.38 mins<br>486 (M + H)⁺ |
| PhCH₂CH₂ | Me | 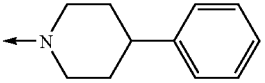 | 3.83 mins<br>390 (M + H)⁺ |
| 3-ClBn | Et | 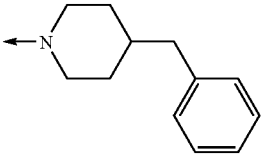 | 4.27 mins<br>438 (M + H)⁺ |
| 3-ClBn | Et | 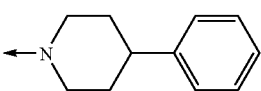 | 4.05 mins<br>424 (M + H)⁺ |
| Bn | Me | 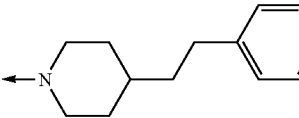 | 4.05 mins<br>404 (M + H)⁺ |
| 2-ClBn | H | 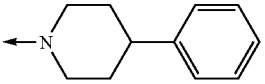 | 3.55 mins<br>396 (M + H)⁺ |
| 2-ClBn | Me | 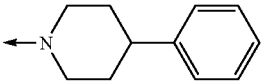 | 3.85 mins<br>410 (M + H)⁺ |
| 3-ClBn | H | 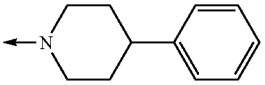 | 3.57 mins<br>396 (M + H)⁺ |
| 4-ClBn | H | 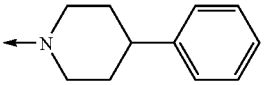 | 3.60 mins<br>396 (M + H)⁺ |
| Bn | Me | 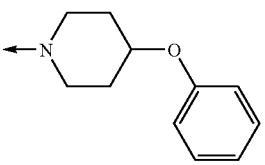 | 3.61 mins<br>392 (M + H)⁺ |
| 3-BrBn | H | 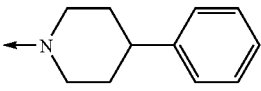 | 3.60 mins<br>440 (M + H)⁺ |

TABLE 1-continued
| R³ | R⁴ | —N(R''')(R'''') | LC-MS (RT, mass(es) found) |
|---|---|---|---|
| Bn | H | 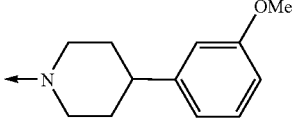 | 3.31 mins 392 (M + H)⁺ |
| 3-OMeBn | H | 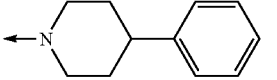 | 3.35 mins 392 (M + H)⁺ |
| Bn | H | 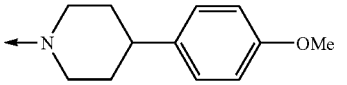 | 3.29 mins 392 (M + H)⁺ |
| Bn | H | 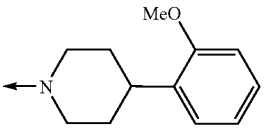 | 3.42 mins 392 (M + H)⁺ |
| Bn | H | 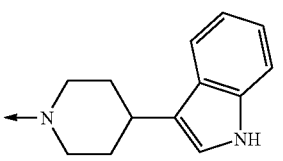 | 3.19 mins 401 (M + H)⁺ |
| Bn | H | 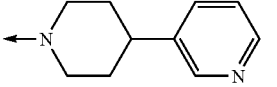 | 1.81 mins 363 (M + H)⁺ |
| Bn | H | 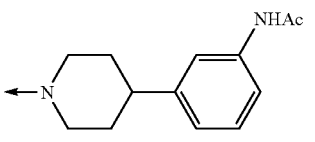 | 2.74 mins 419 (M + H)⁺ |
| Bn | H | 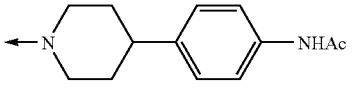 | 2.66 mins 419 (M + H)⁺ |
| 3-CNBn | H | 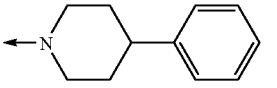 | 3.24 mins 387 (M + H)⁺ |
| 4-CNBn | H | 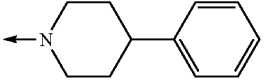 | 3.24 mins 387 (M + H)⁺ |
| Bn | H | 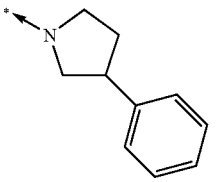 | 3.11 mins 348 (M + H)⁺ |

TABLE 1-continued

| R³ | R⁴ | —N(R''')(R'''') | LC-MS (RT, mass(es) found) |
|---|---|---|---|
| Bn | H | *N-piperidinyl-phenyl* | 3.37 mins<br>362 (M + H)⁺ |
| Bn | H | *4-(4-chlorophenyl)piperazin-1-yl* | 12.67 mins<br>395 (M + H)⁺ |
| Bn | H | *4-(3-chlorophenyl)piperazin-1-yl* | 12.52 mins<br>395 (M + H)⁺ |

Example 5

Glucocorticoid Receptor Binding Assay

The following is a description of an assay for determining the inhibition of dexamethasone binding of the Human Recombinant Glucocorticoid Receptor:

Binding protocol: Compounds were tested in a binding displacement assay using human recombinant glucocorticoid receptor with $^3$H-dexamethasone as the ligand. The source of the receptor was recombinant baculovirus-infected insect cells. This GR was a full-length steroid hormone receptor likely to be associated with heat-shock and other endogenous proteins.

The assay was carried out in v-bottomed 96-well polypropylene plates in a final volume of 200 µl containing 0.5 nM GR solution, 2.5 nM 3H-dexamethasone (Amersham TRK 645) in presence of test compounds, test compound vehicle (for total binding) or excess dexamethasone (20 µM, to determine non-specific binding) in an appropriate volume of assay buffer.

For the Primary Screen, test compounds were tested at 1 µM in duplicate. These compounds were diluted from 10 mM stock in 100% DMSO. After dilution to 100 µM, 5 µl were added to 245 µl assay buffer to obtained 2 µM compound and 2% DMSO.

For the IC$_{50}$ determinations, test compounds were tested at 6 concentrations in duplicate (concentration range depends on % inhibition binding that was obtained in the Primary Screen,). Test compounds were diluted from 10 mM stock in 100% DMSO. The tested solutions were prepared at 2×final assay concentration in 2% DMSO/assay buffer.

All reagents and the assay plate were kept on ice during the addition of reagents. The reagents were added to wells of a v-bottomed polypropylene plate in the following order: 50 µl of 10 nM 3H-dexamethasone solution, 100 µl of TB/NSB/compound solution and 50 µl of 2 nM GR solution. After the additions, the incubation mixture was mixed and incubated for 2.5 hrs at 4° C.

After 2.5 hrs incubation, unbound counts were removed with dextran coated charcoal (DCC) as follows: 25 µl of DCC solution (10% DCC in assay buffer) was added to all wells and mixed (total volume 225 µl). The plate was centrifuged at 4000 rpm for 10 minutes at 4° C. 75 µl of the supernatants (i.e. ⅓ of total volume) was carefully pipetted into an optiplate. 200 µl of scintillation cocktail were added (Microscint-40, Packard Bioscience. B.V.). The plate was vigorously shaken for approx. 10 minutes and counted on Topcount.

For the IC$_{50}$ determinations, the results were calculated as % inhibition [$^3$H]-dexamethasone bound and fitted to sigmoidal curves (fixed to 100 and 0) to obtain IC$_{50}$ values (concentration of compound that displaces 50% of the bound counts). The IC$_{50}$ values were converted to K$_i$ (the inhibition constant) using the Cheng-Prusoff equation. Test results are presented in Table 2 for selected compounds of the Invention. Compounds with a K$_i$ value of <10 nM are designated with *; compounds with a K$_i$ value of 10-100 nM are designated with ; compounds with a K$_i$ of >100 nM are designated with *.

Reagents: Assay buffer: 10 mM potassium phosphate buffer pH 7.6 containing 5 mM DTT, 10 mM sodium molybdate, 100 µM EDTA and 0.1% BSA.

TABLE 2

| NO. | COMPOUND | Ki |
|---|---|---|
| 1 | *pyrimidinedione with 3-(trifluoromethyl)benzyl and 4-hydroxypiperidinyl substituents* | * |

TABLE 2-continued

| NO. | COMPOUND | Ki |
|-----|----------|-----|
| 2 | | * |
| 3 | | * |
| 4 | | ** |

TABLE 2-continued

| NO. | COMPOUND | Ki |
|-----|----------|-----|
| 5 | | ** |
| 6 | | ** |
| 7 | | ** |

TABLE 2-continued
| NO. | COMPOUND | Ki |
|-----|----------|-----|
| 8 | 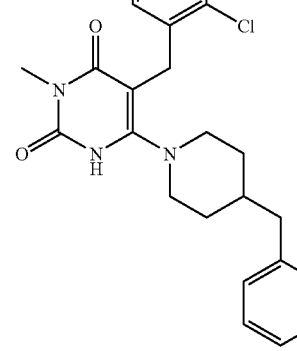 | * |
| 9 | 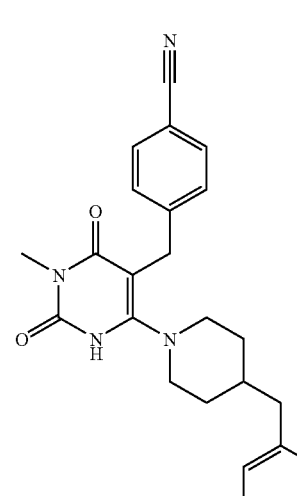 | * |
| 10 | 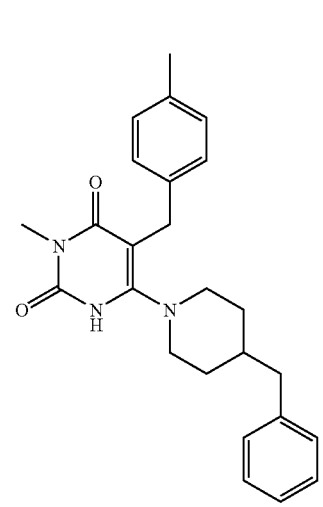 | ** |ода
TABLE 2-continued
| NO. | COMPOUND | Ki |
|-----|----------|-----|
| 11 | 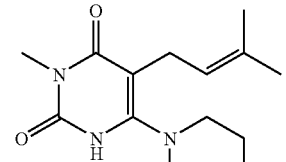 | * |
| 12 | 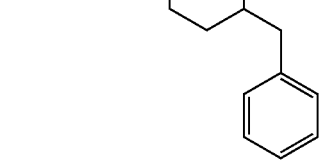 | ** |
| 13 | 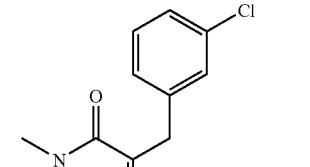 | * |

TABLE 2-continued
| NO. | COMPOUND | Ki |
|---|---|---|
| 14 | 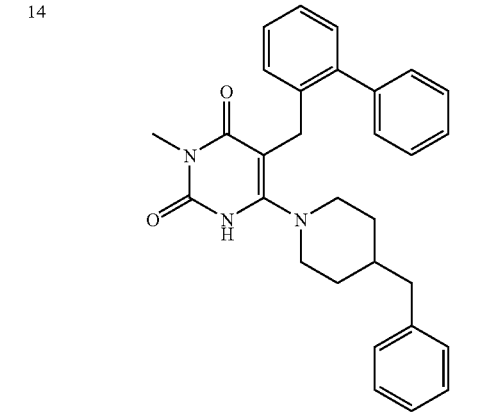 | * |
| 15 | 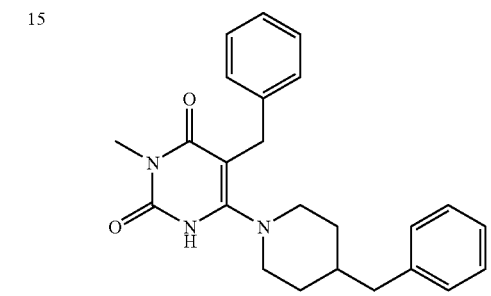 | ** |
| 16 | 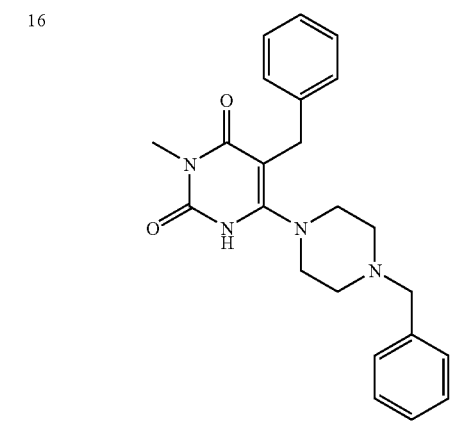 | * |
| 17 | 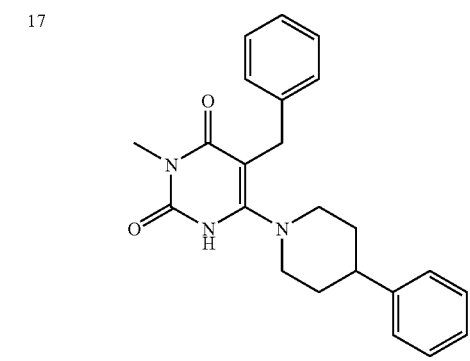 | ** |
TABLE 2-continued
| NO. | COMPOUND | Ki |
|---|---|---|
| 18 | 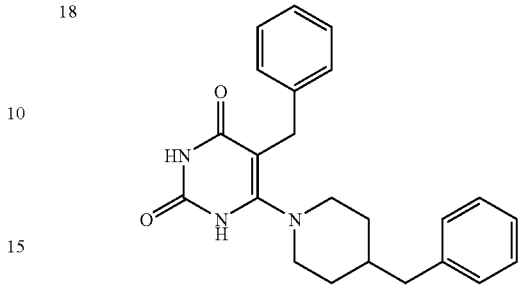 | ** |
| 19 | 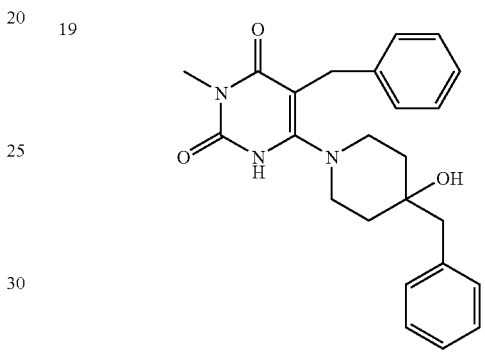 | * |
| 20 | 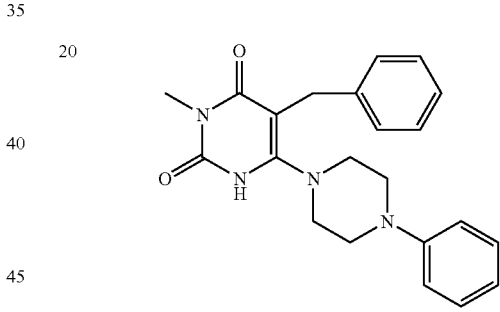 | * |
| 21 | 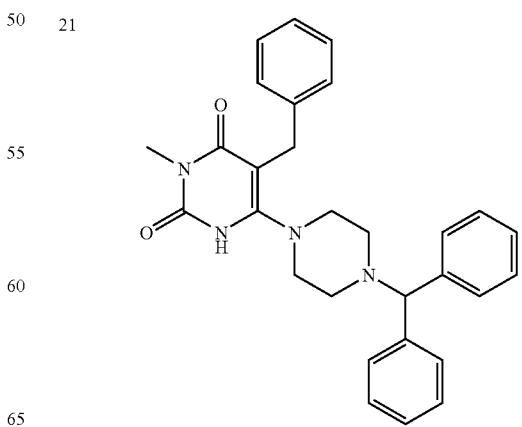 | * |

TABLE 2-continued

| NO. | COMPOUND | Ki |
|---|---|---|
| 22 | | * |
| 23 | | * |
| 24 | | ** |
| 25 | | * |

TABLE 2-continued

| NO. | COMPOUND | Ki |
|---|---|---|
| 26 | | * |
| 27 | | * |
| 28 | | * |
| 29 | | * |

TABLE 2-continued
| NO. | COMPOUND | Ki |
|---|---|---|
| 30 | 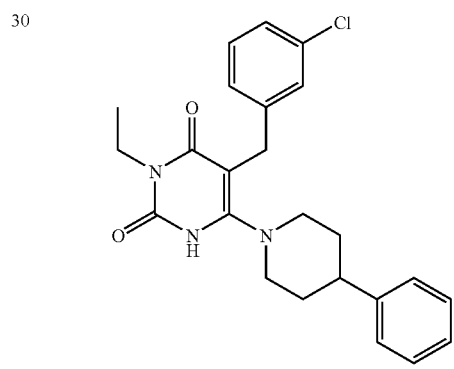 | * |
| 31 | 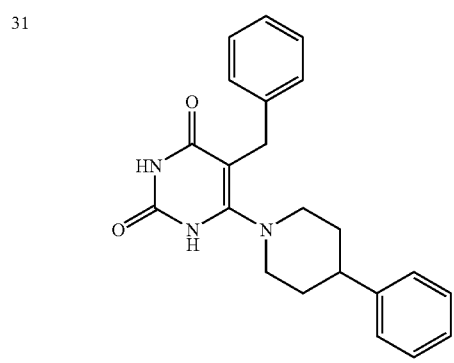 | *** |
| 32 | 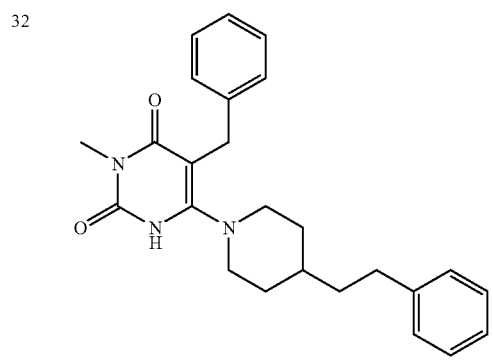 | * |
| 33 | 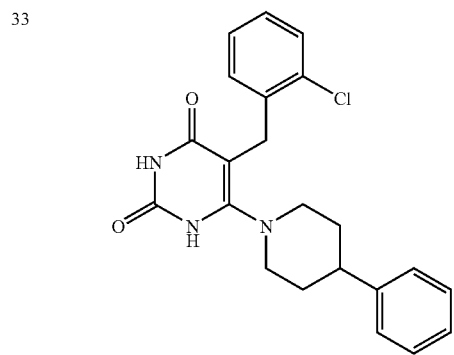 | *** |
TABLE 2-continued
| NO. | COMPOUND | Ki |
|---|---|---|
| 34 | 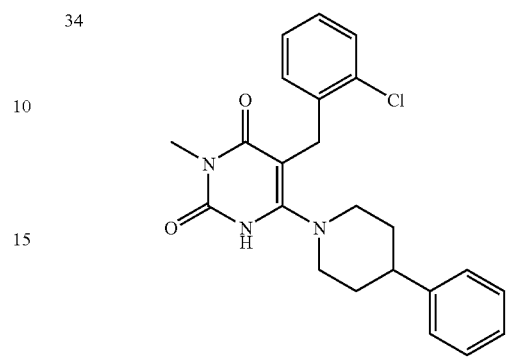 | ** |
| 35 | 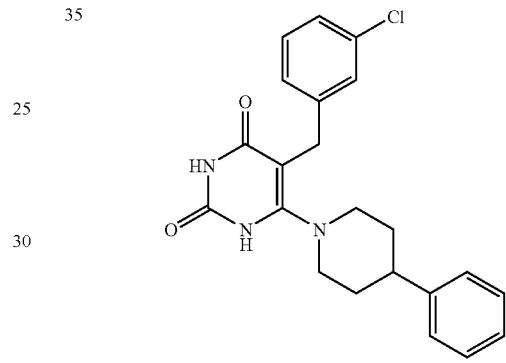 | *** |
| 36 | 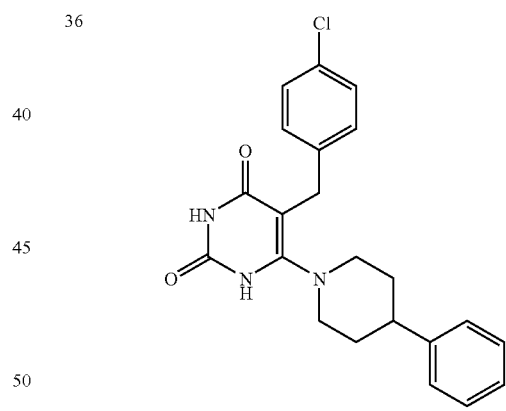 | ** |
| 37 | 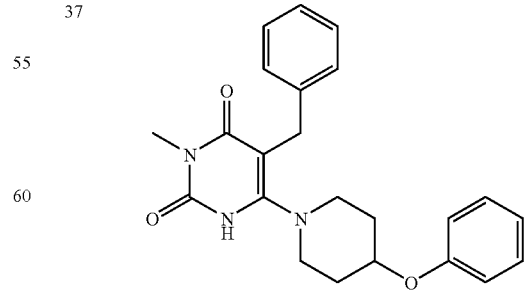 | ** |

TABLE 2-continued
| NO. | COMPOUND | Ki |
|---|---|---|
| 38 | 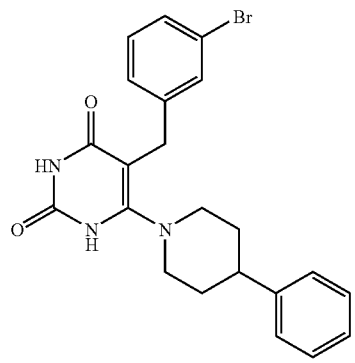 | ** |
| 39 | 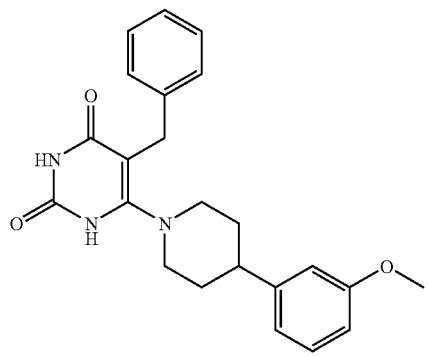 | *** |
| 40 | 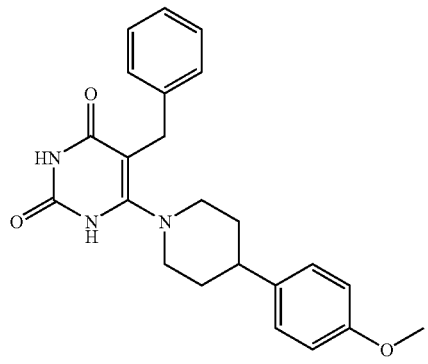 | ** |
| 41 | 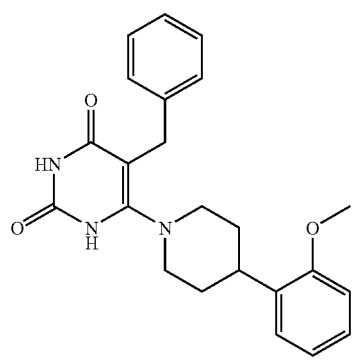 | *** |
TABLE 2-continued
| NO. | COMPOUND | Ki |
|---|---|---|
| 42 | 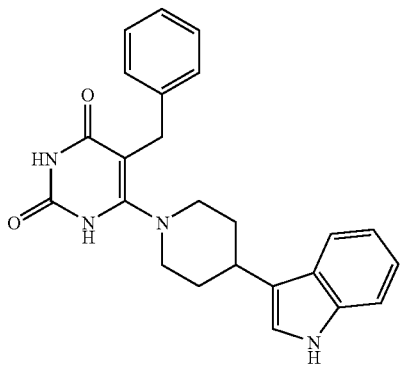 | ** |
| 43 | 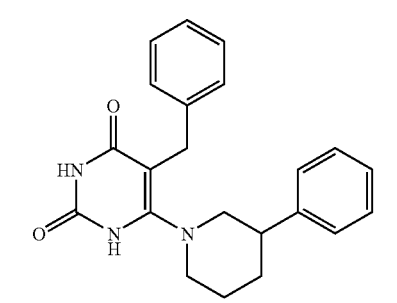 | *** |
| 44 | 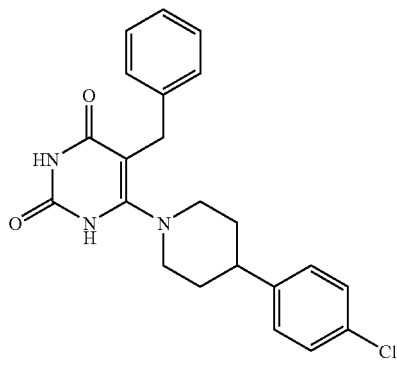 | * |
| 45 | 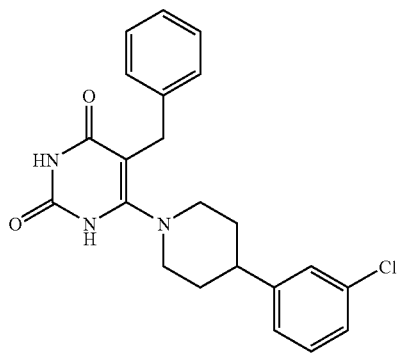 | *** |

TABLE 2-continued

| NO. | COMPOUND | Ki |
|-----|----------|-----|
| 46 | (structure) | ** |
| 47 | (structure) | ** |
| 48 | (structure) | ** |

Example 7

GR Functional Assay Using SW1353/MMTV-5 Cells

SW1353/MMTV-5 is an adherent human chondrosarcoma cell line that contains endogenous glucocorticoid receptors. It was transfected with a plasmid (pMAMneo-Luc) encoding firefly *luciferase* located behind a glucocorticoid-responsive element (GRE) derived from a viral promoter (long terminal repeat of mouse mammary tumor virus). A stable cell line SW1353/MMTV-5 was selected with geneticin, which was required to maintain this plasmid. This cell line was thus sensitive to glucocorticoids (dexamethasone) leading to expression of luciferase ($EC_{50}^{dex}$ 10 nM). This dexamethasone-induced response was gradually lost over time, and a new culture from an earlier passage was started (from a cryo-stored aliquot) every three months.

In order to test for a GR-antagonist, SW1353/MMTV-5 cells were incubated with several dilutions of the compounds in the presence of $5 \times EC_{50}^{dex}$ (50 nM), and the inhibition of induced luciferase expression was measured using a luminescence in a Topcounter (LucLite kit from Perkin Elmer). For each assay, a dose-response curve for dexamethasone was prepared in order to determine the $EC_{50}^{dex}$ required for calculating the $K_i$ from the $IC_{50}$'s of each tested compound. Test results are presented in Table 3 for selected compounds of the invention. Compounds with a $K_i$ value of 10-100 nM are designated with **; compounds with a $K_i$ of >100 nM are designated with *. The compound numbers refer to the chemical structures provided in Table 2 above.

SW1353/MMTV-5 cells were distributed in 96-well plates and incubated in medium (without geneticin) for 24 hrs (in the absence of $CO_2$). Dilutions of the compounds in medium+50 nM dexamethasone were added and the plates further incubated for another 24 hrs after which the luciferase expression is measured.

TABLE 3

| COMPOUND | Ki |
|----------|-----|
| 31 | ** |
| 33 | ** |
| 34 | * |
| 35 | ** |
| 36 | * |
| 38 | ** |
| 43 | * |
| 45 | ** |

Example 8

Cytotoxicity Assay Using SW1353/Luc-4 Cells

In order to exclude the possibility that compounds inhibit the dexamethasone-induced luciferase response (GR-antagonist) due to their cytotoxicity or due to their direct inhibition of luciferase, a SW1353 cell line was developed that constitutively expresses firefly luciferase, by transfection with plasmid pcDNA3.1-Luc and selection with geneticin. The cell line SW1353/Luc-4 was isolated that constitutively expresses luciferase.

SW1353/Luc-4 are distributed in 96-well plates and incubated (no $CO_2$) for 24 hrs, after which compound dilutions (without dexamethasone) are added. After a further 24 hrs incubations, luciferase expression is measured using the "LucLite" assay.

Example 9

MR and PR Functional Assays Using T47D/MMTV-5 Cells

T47D/MMTV-5 is an adherent human breast carcinoma cell line containing endogenous mineralocorticoid—MR) and progesterone (PR) receptors. As for the SW1353 cell line, T47D cells have been transfected with the same pMAMneo-Luc plasmid, and stable lines selected with geneticin. A cell line T47D/MMTV-5 was isolated which responds to aldosterone ($EC_{50}^{ald}$ 100 nM), and progesterone ($EC_{50}^{prog}$ 10 nM), leading to expression of luciferase.

As for the GR assay to test for MR- or PR-antagonists, the T47D/MMTV-5 cells are incubated with several dilutions of the compounds in the presence of the 5×EC$_{50}$ of the agonist aldosterol (EC$_{50}^{ald}$ 100 nM) or progesterone (EC$_{50}^{prog}$ 10 nM) respectively. For each assay, a dose response curve is prepared for both aldosterone and progesterone.

T47D/MMTV-5 cells are distributed in 96-well plates (100 μl) in RPM11640 medium +10% Charcoal stripped FCS. The cells are incubated for 24 hrs in the CO$_2$-oven. A volume of 100 μl of the compound dilutions in medium+agonist (500 nM aldost; 50 nM progest) are added, and the plates further incubated for another 24 hrs after which the luciferase expression is measured.

Example 10

Selectivity Binding Assays

Selectivity binding assays were performed against human estrogen (ERα), progesterone (PR), androgen (AR) and mineralocorticoid (MR) receptors. The selectivity assays were carried out in the same assay buffer and volumes as the GR binding assay and DCC was used to separate free from bound label.

Mineralocorticoid binding assay: MR was obtained from Sf9 cells infected with recombinant baculovirus containing MR, and the MR was isolated according to the method of Binart et al (Binart, N.; Lombes, M.; Rafestin-Oblin, M. E.; Baulieu, E. E. Characterisation of human mineralocorticoid receptor expressed in the baculovirus system. *PNAS US,* 1991, 88, 10681-10685). Compounds were tested against an appropriate dilution of the MR (determined for each batch of receptor) with 2.4 nM of [$^3$H] aldosterone (Perkin Elmer NET419) and incubated for 60 mins at room temperature.

Estrogen binding assay: Compounds were tested for displacement of 0.56 nM [$^3$H]-estradiol (Perkin Elmer NET517) binding to 0.5 nM ERα (obtained from PanVera 26467A) following an incubation period of 90 mins at room temperature.

Progesterone binding assay: Compounds were tested for displacement of 3 nM [$^3$H]-progesterone (Perkin Elmer NET381) binding to 1 nM PR (obtained from PanVera 24900). This assay was incubated for 120 mins at 4° C.

Androgen binding assay: Compounds were tested, in triplicate, for displacement of 6 nM [$^3$H]-dihydrotestosterone (Perkin Elmer NET453) binding to 3 nM PR (obtained from PanVera 24938). This assay was incubated overnight at 4° C.

Selected compounds of Table 2 were tested against MR, ER, PR, and AR receptors. All compounds tested showed Ki's of greater than 100 nM for MR, ER, PR, and/or AR receptors.

What is claimed is:

1. A compound having the formula:

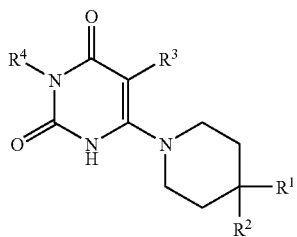

wherein,
R$^1$ is a member selected from unsubstituted phenyl and phenyl substituted with R$^{1B}$;
R$^2$ is a member selected from hydrogen, —CN, and —OH,
R$^3$ is a member selected from unsubstituted benzyl and benzyl substituted with R$^{3A}$;
R$^{3A}$ and R$^{1B}$ are members independently selected from halogen, hydrogen, unsubstituted alkyl, unsubstituted heteroalkyl, unsubstituted cycloalkyl, unsubstituted heterocycloalkyl, unsubstituted aryl, unsubstituted heteroaryl, —CN, —CF$_3$, —OR$^5$, —SR$^6$, —NR$^7$R$^8$, -L$^3$—C(O)R$^9$, and -L$^4$—S(O)$_2$R$^{10}$, wherein
R$^5$, R$^6$, R$^7$, and R$^8$ are members independently selected from hydrogen, unsubstituted alkyl, unsubstituted heteroalkyl, unsubstituted cycloalkyl, unsubstituted heterocycloalkyl, unsubstituted aryl, and unsubstituted heteroaryl, wherein
R$^7$ and R$^8$ are optionally joined to form a ring with the nitrogen to which they are attached,
R$^9$ R$^{10}$ are members independently selected from hydrogen, unsubstituted alkyl, unsubstituted heteroalkyl, unsubstituted cycloalkyl, unsubstituted heterocycloalkyl, unsubstituted aryl, unsubstituted heteroaryl, and —NR$^{11}$R$^{12}$, wherein
R$^{11}$ and R$^{12}$ are independently selected from the hydrogen, unsubstituted alkyl, unsubstituted heteroalkyl, unsubstituted cycloalkyl, unsubstituted heterocycloalkyl, unsubstituted aryl, unsubstituted heteroaryl, and
L$^3$ and L$^4$ are members independently selected from a bond and —NH—; and
R$^4$ is a member selected from hydrogen and unsubstituted alkyl;
wherein
each aryl is independently selected from the group consisting of phenyl, 1-naphthyl, 2-naphthyl, and 4-biphenyl,
each heterocycloalkyl is independently selected from the group consisting of 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, and 2-piperazinyl, and
each heteroaryl is independently selected from the group consisting of 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

2. The compound of claim 1, wherein each unsubstituted alkyl is an unsubstituted C$_1$-C$_{20}$ alkyl, each unsubstituted heteroalkyl is an unsubstituted 2 to 20 membered heteroalkyl, each unsubstituted cycloalkyl is an unsubstituted C$_4$-C$_8$ cycloalkyl, each unsubstituted heterocycloalkyl is an unsubstituted 4 to 8 membered heterocycloalkyl, each unsubstituted alkylene is an unsubstituted C$_1$-C$_{20}$ alkylene, each unsubstituted heteroalkylene is an unsubstituted 2 to 20 membered heteroalkylene, each unsubstituted arylalkyl is an unsubstituted C$_1$-C$_{20}$ arylalkyl, each unsubstituted heteroarylalkyl is an unsubstituted C$_1$-C$_{20}$ heteroarylalkyl, each unsubstituted cycloalkyl-alkyl is an unsubstituted C$_1$-C$_{20}$ cycloalkyl-alkyl, and each unsubstituted heterocycloalkyl-alkyl is an unsubstituted C$_1$-C$_{20}$ heterocycloalkyl-alkyl.

3. The compound of claim 1, wherein R$^4$ is a member selected from hydrogen and unsubstituted C$_1$-C$_5$ alkyl.

4. The compound of claim 1, wherein R⁴ hydrogen.

5. The compound of claim 1, wherein R¹ is unsubstituted phenyl.

6. The compound of claim 1, wherein R² is hydrogen.

7. The compound of claim 1, wherein said compound has the formula

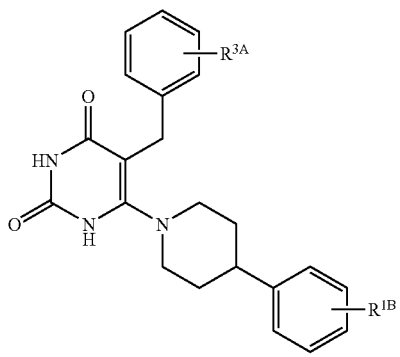

(II)

8. The compound of claim 7, wherein each unsubstituted alkyl is an unsubstituted $C_1$-$C_{20}$ alkyl, each unsubstituted heteroalkyl is an unsubstituted 2 to 20 membered heteroalkyl, each unsubstituted cycloalkyl is an unsubstituted $C_4$-$C_8$ cycloalkyl, each unsubstituted heterocycloalkyl is an unsubstituted 4 to 8 membered heterocycloalkyl, each unsubstituted alkylene is an unsubstituted $C_1$-$C_{20}$ alkylene, and each unsubstituted heteroalkylene is an unsubstituted 2 to 20 membered heteroalkylene.

9. A pharmaceutical composition for treating a disorder or condition through modulating a glucocorticoid receptor in a subject in need of such treatment, said composition comprising a pharmaceutically acceptable excipient and an effective amount of a compound of claim 1.

10. The pharmaceutical composition of claim 9, comprising from 1 to 2000 milligrams of said compound.

11. The pharmaceutical composition of claim 9, wherein said compound is adapted for oral administration.

12. The pharmaceutical composition of claim 9, in the form of a tablet.

* * * * *